US012616576B2

(12) United States Patent　(10) Patent No.:　US 12,616,576 B2

Gorhe et al.　(45) **Date of Patent:　*May 5, 2026**

(54) METHODS OF MODIFYING THE POROUS SURFACE OF IMPLANTS

(71) Applicant: Biomet Manufacturing, LLC, Warsaw, IN (US)

(72) Inventors: Devendra Gorhe, Warsaw, IN (US); Donald L. Yakimicki, Warsaw, IN (US); Philip McBride, Denver, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/853,443

(22) Filed: Jun. 29, 2022

(65) Prior Publication Data

US 2022/0331115 A1　Oct. 20, 2022

Related U.S. Application Data

(63) Continuation of application No. 17/151,352, filed on Jan. 18, 2021, now Pat. No. 11,395,740, which is a
(Continued)

(51) Int. Cl.
*A61F 2/30*　(2006.01)
*A61L 27/06*　(2006.01)
(Continued)

(52) U.S. Cl.
CPC .......... *A61F 2/30767* (2013.01); *A61L 27/06* (2013.01); *A61L 27/306* (2013.01); *A61L 27/54* (2013.01); *A61L 27/56* (2013.01); *C25D*

*11/022* (2013.01); *C25D 11/024* (2013.01); *C25D 11/026* (2013.01); *C25D 11/20* (2013.01);
(Continued)

(58) Field of Classification Search
CPC ..................................................... C25D 11/026
See application file for complete search history.

(56) References Cited

U.S. PATENT DOCUMENTS 5,478,237 A　12/1995　Ishizawa
5,616,229 A　4/1997　Samsonov et al.
(Continued)

FOREIGN PATENT DOCUMENTS

CN　101139730 A　3/2008
CN　102425000 A　4/2012
(Continued)

OTHER PUBLICATIONS

Machine translation of WO-9638603-A1, (1996).
(Continued)

*Primary Examiner* — Brian W Cohen
(74) *Attorney, Agent, or Firm* — Schwegman Lundberg & Woessner, P.A.

(57) ABSTRACT

Methods are provided for modifying a porous surface of an implantable medical device by subjecting the porous surface to a modified micro-arc oxidation process to improve the ability of the medical device to resist microbial growth, to improve the ability of the medical device to adsorb a bioactive agent or a therapeutic agent, and to improve tissue in-growth and tissue on-growth of the implantable medical device.

21 Claims, 16 Drawing Sheets

Related U.S. Application Data continuation of application No. 15/940,382, filed on Mar. 29, 2018, now Pat. No. 10,893,944.

(60) Provisional application No. 62/478,821, filed on Mar. 30, 2017.

(51) Int. Cl.

| | |
|---|---|
| *A61L 27/30* | (2006.01) |
| *A61L 27/32* | (2006.01) |
| *A61L 27/54* | (2006.01) |
| *A61L 27/56* | (2006.01) |
| *C25D 11/02* | (2006.01) |
| *C25D 11/20* | (2006.01) |
| *C25D 11/26* | (2006.01) |
| *C25D 13/02* | (2006.01) |
| *C25D 13/04* | (2006.01) |
| *C25D 17/02* | (2006.01) |

(52) U.S. Cl.
CPC .............. *C25D 11/26* (2013.01); *C25D 13/02* (2013.01); *C25D 13/04* (2013.01); *C25D 17/02* (2013.01); *A61F 2310/00023* (2013.01); *A61F 2310/00796* (2013.01); *A61L 27/32* (2013.01); *A61L 2400/18* (2013.01)

(56) References Cited

U.S. PATENT DOCUMENTS

| | | | |
|---|---|---|---|
| 6,197,178 B1 | 3/2001 | Patel et al. | |
| 7,695,522 B2 | 4/2010 | Pickford et al. | |
| 7,708,558 B1 | 5/2010 | Hall et al. | |
| 7,906,132 B2 | 3/2011 | Ziegler et al. | |
| 7,998,568 B2 | 8/2011 | Raja et al. | |
| 8,100,985 B2 | 1/2012 | Hall | |
| 8,858,775 B2 | 10/2014 | Agg et al. | |
| 8,888,083 B2 | 11/2014 | Hosaka | |
| 8,945,363 B2 | 2/2015 | Pickford et al. | |
| 8,992,596 B2 | 3/2015 | Bayer et al. | |
| 9,011,665 B2 | 4/2015 | Pickford et al. | |
| 9,045,843 B2 * | 6/2015 | Andreacchi | C25F 3/16 |
| 9,090,250 B2 | 7/2015 | Sujan et al. | |
| 9,096,943 B2 | 8/2015 | Shawcross et al. | |
| 9,255,340 B1 * | 2/2016 | Adkisson | C25D 17/12 |
| 9,393,349 B2 | 7/2016 | Pickford et al. | |
| 10,893,944 B2 | 1/2021 | Gorhe et al. | |
| 11,395,740 B2 | 7/2022 | Gorhe et al. | |
| 2004/0149586 A1 | 8/2004 | Sul | |
| 2006/0091020 A1 | 5/2006 | Hossick-Schott et al. | |
| 2008/0086195 A1 | 4/2008 | Atanasoka et al. | |
| 2008/0251391 A1 * | 10/2008 | Benco | A61L 31/10 204/242 |
| 2009/0086195 A1 | 4/2009 | Effenhauser et al. | |
| 2009/0112310 A1 * | 4/2009 | Zhang | A61L 31/146 623/1.42 |
| 2011/0022162 A1 | 1/2011 | Radhakishnan et al. | |
| 2011/0313539 A1 | 12/2011 | Tsuchiya et al. | |
| 2012/0053679 A1 * | 3/2012 | Fircho | A61L 31/088 205/640 |
| 2012/0119591 A1 * | 5/2012 | Sun | C25D 11/026 307/154 |
| 2012/0150295 A1 | 6/2012 | Dingeldein et al. | |
| 2013/0116696 A1 | 5/2013 | Imwinkelried et al. | |
| 2013/0221816 A1 | 8/2013 | Liou et al. | |
| 2013/0319869 A1 | 12/2013 | Turner | |
| 2014/0318974 A1 | 10/2014 | Curran et al. | |
| 2015/0110844 A1 | 4/2015 | Pickford et al. | |
| 2015/0140314 A1 | 5/2015 | Tao et al. | |
| 2016/0345451 A1 * | 11/2016 | Wu | C25D 15/00 |
| 2017/0167043 A1 * | 6/2017 | Weng | C25D 11/24 |
| 2018/0280143 A1 | 10/2018 | Gorhe et al. | |
| 2018/0291520 A1 | 10/2018 | Golding et al. | |
| 2021/0186703 A1 | 6/2021 | Gorhe et al. | |

FOREIGN PATENT DOCUMENTS

| | | | | |
|---|---|---|---|---|
| GB | 2142654 A | 1/1985 | | |
| JP | H10158888 A | 6/1998 | | |
| WO | WO-9638603 A1 | 12/1996 | | |
| WO | WO-2010106164 A1 | 9/2010 | | |
| WO | WO-2010119443 A1 * | 10/2010 | ............. | C09D 5/448 |

OTHER PUBLICATIONS

"U.S. Appl. No. 15/940,382, Final Office Action mailed Mar. 9, 2020", 18 pgs.

"U.S. Appl. No. 15/940,382, Non Final Office Action mailed Oct. 7, 2019", 18 pgs.

"U.S. Appl. No. 15/940,382, Notice of Allowance mailed Sep. 22, 2020", 11 pgs.

"U.S. Appl. No. 15/940,382, Response filed Jan. 2, 2020 to Non Final Office Action mailed Oct. 7, 2019", 11 pgs.

"U.S. Appl. No. 15/940,382, Response filed Jun. 9, 2020 to Final Office Action mailed Mar. 9, 2020", 13 pgs.

"U.S. Appl. No. 15/940,382, Response filed Aug. 12, 2019 to Restriction Requirement mailed Jun. 12, 2019", 6 pgs.

"U.S. Appl. No. 15/940,382, Restriction Requirement mailed Jun. 12, 2019", 5 pgs.

"U.S. Appl. No. 17/151,352, Non Final Office Action mailed Oct. 18, 2021", 19 pgs.

"U.S. Appl. No. 17/151,352, Notice of Allowance mailed Mar. 25, 2022", 10 pgs.

"U.S. Appl. No. 17/151,352, Preliminary Amendment Filed Mar. 15, 2021", 5 pgs.

"U.S. Appl. No. 17/151,352, Response filed Jan. 12, 2022 to Non Final Office Action mailed Oct. 18, 2021", 10 pgs.

"U.S. Appl. No. 17/151,352, Response filed Sep. 8, 2021 to Restriction Requirement mailed Jul. 14, 2021", 6 pgs.

"U.S. Appl. No. 17/151,352, Restriction Requirement mailed Jul. 14, 2021", 5 pgs.

"European Application Serial No. 18165248.8, Communication Pursuant to Article 94(3) EPC mailed Jan. 16, 2020", 5 pgs.

"European Application Serial No. 18165248.8, Extended European Search Report mailed Nov. 30, 2018", 11 pgs.

"European Application Serial No. 18165248.8, Partial Supplementary European Search Report mailed Aug. 30, 2018", 13 pgs.

"European Application Serial No. 18165248.8, Response filed May 26, 20 to Communication Pursuant to Article 94(3) EPC mailed Jan. 16, 2020", 12 pgs.

"European Application Serial No. 18165248.8, Response filed Jul. 2, 2019 to Office Action mailed Jan. 7, 2019", 9 pgs.

"European Application Serial No. 21168162.2, Extended European Search Report mailed Mar. 3, 2022", 9 pgs.

Aliasghari, Sepideh, "Plasma Electrolytic Oxidation of Titanium", A thesis submitted to The University of Manchester for the degree of Doctor of Philosophy in the Faculty of Engineering and Physical Sciences, (2014), 223.

Cimenoglu, Huseyin, et al., "Micro-arc oxidation of Ti6Al4V and Ti6Al7Nb alloys for biomedical applications", Materials Characterization 62, 304-311, (Mar. 2011), 9 pgs.

Dicu, M., et al., "Synthesis and properties of the porous titania coatings formed on titanium by plasma electrolytic oxidation for biomedical application", Journal of Optoelectronics and Advanced Materials vol. 13, No. 3, Mar. 2011, p. 324-331, (2011), 8 pgs.

Gallo, Jiri, et al., "Antibacterial Surface Treatment for Orthopaedic Implants", Int. J. Mol. Sci. 2014, 15, 13849-13880; doi:10.3390/ijms150813849, (2014), 32 pgs.

Goodman, Stuart B., et al., "The Future of Biologic Coatings for Orthopaedic Implants", Biomaterials. Apr. 2013 ; 34(13): 3174-3183. doi:10.1016/j.biomaterials.2013.01.074., (2013), 20 pgs.

Han, Yong, et al., "Synthesis of nanocrystalline titania films by micro-arc oxidation", Materials Letters 56 (2002) 744-747, (2002), 4 pgs.

Han, Yong, et al., "UV-enhanced bioactivity and cell response of micro-arc oxidized titania coatings", Acta Biomaterialia 4 (2008) 1518-1529, (2008), 12 pgs.

(56) References Cited

OTHER PUBLICATIONS

He, Xiaojing, et al., "Review of Antibacterial Activity of Titanium-Based Implants' Surfaces Fabricated by Micro-Arc Oxidation", Coatings, vol. 7, No. 3, (Mar. 1, 2017).

Li, Long-Hao, et al., "Improved biological performance of Ti implants due to surface modification by micro-arc oxidation", Biomateri, Elsevier Science Publishers BV., Barking, GB, vol. 25, No. 14, (Jun. 1, 2004), 2867-2875.

Raphel, Jordan, et al., "Multifunctional Coatings to Simultaneously Promote Osseointegration and Prevent Infection of Orthopaedic Implants", Biomaterials. Apr. 2016 ; 84: 301-314. doi:10.1016/j.biomaterials.2016.01.016, (2016), 33 pgs.

Romano, Carlo Luca, et al., "Antibacterial coating of implants in orthopaedics and trauma: a classification proposal in an evolving panorama", Journal of Orthopaedic Surgery and Research (2015) 10:157 DOI 10.1186/s13018-015-0294-5, (2015), 11 pgs.

"European Application Serial No. 21168162.2, Response filed Oct. 13, 2022 to Extended European Search Report mailed Mar. 3, 2022", 19 pgs.

"European Application Serial No. 21168162.2, Communication Pursuant to Article 94(3) EPC mailed Aug. 11, 2023", 7 pgs.

"European Application Serial No. 21168162.2, Communication Pursuant to Article 943 EPC mailed Oct. 7, 2025", 6 pgs.

* cited by examiner

METHODS OF MODIFYING THE POROUS SURFACE OF IMPLANTS

CLAIM OF PRIORITY

This application is a continuation of U.S. application Ser. No. 17/151,352, filed Jan. 18, 2021, which is a continuation of U.S. application Ser. No. 15/940,382, filed Mar. 29, 2018, now issued as U.S. Pat. No. 10,893,944, which claims the benefit of U.S. Provisional Patent Application Ser. No. 62/478,821, filed on Mar. 30, 2017, the benefit of priority of each of which is claimed hereby, and each of which is incorporated by reference herein in its entirety.

FIELD

The present disclosure relates to medical devices, and particularly to implantable medical devices having modified porous surfaces, and methods of modifying the porous surfaces of implantable medical devices using modified micro-arc oxidation processing.

BACKGROUND

This section provides background information related to the present disclosure, which is not necessarily prior art.

Implantable medical devices (also referred to herein as a medical implant or implant) are routinely used in orthopedic, trauma and other surgeries, e.g. prosthetic implants (implants for orthopedic, dental/orthodontal, maxillofacial, trauma, or plastic surgery), nails, screws, pins, wires, plates, external and internal fixators, valves, artificial blood vessels, shunts, stents, catheters and other endoprostheses. Examples of biocompatible materials used in implantable medical devices include polymers, ceramics, aluminum, vanadium, tantalum, iron, titanium, titanium alloys (e.g., Ti6Al4V, Ti6Al7Nb), stainless steels, alloys of nickel, niobium, cobalt, molybdenum, and chromium, Co—Cr alloys, magnesium, and other metals and metal alloys. However, medical implants formed of metals or metal alloys cannot be chemically bonded to tissue, resulting in the formation of gaps and loosening of the implant over the time of use. A medical implant formed of metals or metal alloys can be processed to create surface modifications to improve fixation of the implant in tissue. Medical implants can be modified to have roughened or porous coatings or surfaces (roughened coatings and surfaces may also be referred to herein, collectively, as "porous surfaces"), and such modified implants are particularly useful for medical interventions where tissue in-growth or tissue on-growth is desired to fix the implant within the body. However, roughened or porous coatings and surfaces can create additional surface area for bacterial adherence and growth on the medical implant.

Implant-related infections remain a leading cause for treatment failure and are associated with significant economic and social costs. Biofilm formation, a critical event in the development of implant-related infection, begins immediately after bacterial adhesion on an implant and effectively protects the adhered microorganisms from the host immune response and from antibiotics and other antimicrobial pharmaceutical interventions. Efforts to reduce implant-related infection have focused on the ability of implant surface modifications to minimize bacterial adhesion, inhibit biofilm formation, and/or provide effective bacterial killing to protect implanted medical devices.

Medical implants are known to have anodized surfaces for advantageously receiving a deposit of antimicrobial agents, such as metallic elements and metallic ions, and antimicrobial compositions containing metallic elements or metallic ions, e.g., copper and silver. Such devices and methods of forming such devices are disclosed, for example, in: U.S. Pat. Nos. 7,695,522; 8,858,775; 8,888,983; 8,945, 363; 9,080,250; 9,096,943; and 9,393,349; U.S. Patent Pub. No. 2013/0319869; U.S. Patent Pub. No. 2015/0110844; and U.S. Patent Pub. No. 2015/0299865. Medical implants are also known to have anodized surfaces for deposition of other antimicrobial agents, e.g. iodine and compositions comprising iodine, e.g., U.S. Patent Pub. No. 2011/0313539, which is suitable for medical implants having smooth surfaces that do not facilitate tissue in-growth or tissue on-growth. However, these methods do not provide the desired surface modification on a medical implant having a porous surface or porous coating. Because of their extensive surface area, porous medical implant surfaces and porous coatings on implant surfaces draw large electrical currents when the implant is subjected to standard anodization. These large electrical currents generate heat and prevent or diminish oxidation of the porous surface or porous coating. The potential crevices in porous surfaces of medical implants may result in active dissolution of the anode, which also prevents oxide formation. Such problems can be avoided by masking the roughened or porous surface or coating on the implant to diminish the large draw of current by such surfaces. However, the masked portions of the implant will not become anodized and will, therefore, not advantageously adsorb the antimicrobial or other therapeutic agent.

Micro-arc oxidation (also known as plasma electrolytic oxidation, spark anodization deposition, or spark anodizing) is a variation of traditional electrochemical methods, combining electrochemical oxidation with a high voltage spark treatment to form a ceramic coating on a metal or alloy surface. See, e.g. Dicu, M. et al., *Synthesis and properties of the porous titania coatings formed on titanium by plasma electrolytic oxidation for biomedical application*, J. Optoelectronics and Advance Materials (2011); 13(2):324-331. In standard micro-arc oxidation processing, the sample to be processed is electrically connected, becoming an electrode. A base metal, e.g., a sheet of metal, or a metal cell wall of the electrolyte container, is used as a cathode. The sample is immersed in a suitable electrolyte, at room temperature, and high voltage (e.g., between 100 V to 1000 V) is applied between the anode and cathode, resulting in electrical discharge, sparking or arcing at the sample surface.

A porous medical implant treated by a standard micro-arc oxidation process is illustrated in FIGS. 1A and 1B. A standard anodization process can include processing a metallic device in an acid bath, e.g., a sulfuric acid and phosphoric acid mixture, at room temperature. As shown in FIGS. 1A and 1B, when applied to a porous surface, the standard micro-arc oxidation process does not result in micro-pore formation. Instead, dissolution of the metal and crevice attack on the metal results from standard micro-arc oxidation processing of a porous medical device. During standard micro-arc oxidation processing of a porous medical device, the anodization current remains high throughout the processing, or only slowly decreases. In some instances, the anodization current can increase during processing, indicating that the oxide dissolution rate is greater than oxide formation rate, preventing formation of an oxide layer on the porous medical device.

Many medical implants comprise both smooth surfaces and porous surfaces. Because of the differences in the surface area of smooth surfaces and porous surfaces, application of standard electrolytic reactions to deposit a bioactive agent or a therapeutic agent on such medical implants can result in different amounts of the bioactive agent or therapeutic agent being adsorbed by the smooth surfaces and the porous surfaces of the implant.

It would be useful to provide a porous implantable medical device having an improved porous surface or porous coating that can more effectively receive a deposit of a bioactive agent or a therapeutic agent, e.g. growth factors, osteoconductive agents, osteoinductive agents, proteins, peptides, antibiotics, antimicrobial metallic elements, metallic ions, iodine or other antimicrobial agents to deter microbial attachment, microbial growth and/or biofilm formation. It would also be useful to provide a porous implantable medical device having a modified porous surface for improved tissue in-growth and tissue on-growth. It would also be useful to provide methods of modifying the surface of a porous medical implant to increase the surface area of the porous surface, modify the surface tension of the porous surface, and to prepare the porous surface for more effective deposit of a therapeutic agent or other surface coating.

Overview

This section provides a general summary of the disclosure, and is not a comprehensive disclosure of its full scope or all of its features.

There is provided a method of modifying a porous surface of a metallic medical implant (e.g., a roughened implant surface, a porous implant surface, or an implant surface having a rough coating or a porous coating deposited thereon). In an example, the method can include immersing the porous surface of the medical implant in an electrolyte solution having temperature of about 10° C. of less, and applying a voltage sufficient to cause micro-arc oxidation at the porous surface of the implant to form micro-pores in the surfaces defining the pores (macro-pores) of the porous surface of the medical implant. The porous surface of a medical implant may optionally be modified before immersion in the electrolyte solution by applying a metallic composition to the porous surface of the implant such that the pores of the porous surface are at least partially filled with the metallic composition. There is further provided a method of modifying a porous surface of a medical implant by immersing the porous surface of the implant in an acidic or alkaline electrolyte solution that includes a glycol, an emulsifier, a dispersant, a surfactant, or a combination thereof, and applying a voltage sufficient to cause micro-arc oxidation at the porous surface to form micro-pores in surfaces defining the pores of the porous implant surface. These methods of modifying a porous surface of an implantable medical device can optionally include one or more of: (a) applying a pulsed electrical waveform having a peak voltage between 100 volts and 500 volts, for a period of time between about 1 millisecond to about 50 milliseconds, and at a frequency between about 10 Hz and about 150 Hz; (b) maintaining the temperature of the electrolyte solution at about 10° C. or less throughout the processing, e.g., by circulating the electrolyte through a cooling device or a heat exchanger; (c) vigorously agitating the electrolyte during the processing; (d) applying an ultrasonic wave to the electrolyte solution during the processing; (e) applying a masking material to one or more portions of the implant surface before processing the implant surface in the electrolyte solution to prevent micro-arc oxidation of the masked portions of the implant surface; and (f) providing a counterelectrode (cathode) base metal having a surface area that is preferably larger than the surface area of the medical implant. The modified porous surface of the porous medical implant can readily adsorb one or more bioactive or therapeutic agents, e.g., growth factors, osteoconductive or osteoinductive agents, antimicrobial agents (antibiotics, antimicrobial metal ions, etc.), analgesics, or other drugs.

There are also provided methods of manufacturing a plurality of implantable medical devices having modified porous surfaces (e.g., a roughened substrate surface, a porous substrate surface, or a substrate surface having a rough coating or a porous coating), including securing an anode electrode to each one of a plurality of porous implantable medical devices, immersing the plurality of porous implantable medical devices in an electrolyte solution at a temperature of about 10° C. or less, and sequentially applying an electrical signal to each one of the plurality of implantable medical devices sufficient to cause micro-arc oxidation at the surface of the implant, and controlling the voltage, current and/or the timing of application of the electrical signal to each one of the plurality of implants using a controller.

There are also provided improved methods of depositing one or more bioactive or therapeutic agents on surfaces (smooth surfaces and porous surfaces) of a medical implant by selective application of a cathode to an electrolytic reaction (referred to herein as a "variable cathode method"), such that (i) the cathode is selectively immersed in the electrolyte solution and removed from the electrolyte solution at various times during the reaction, or (ii) the cathode is only partially immersed in the electrolyte solution, based upon the surface area requirement of the medical device, or (iii) the cathode is repeatedly switched on for a period of time and switched off for a period of time throughout the electrolytic reaction. Because a cathode is used to complete an electrical circuit in an electrolytic reaction, varying either the surface area of the cathode in the reaction, or completely switching the cathode on/off at various times during the reaction, the amount of a therapeutic or bioactive agent deposited on the smooth surface and porous surface of a medical implant can be controlled.

There are also provided improved systems and methods to deposit one or more bioactive or therapeutic agents on the smooth surfaces, porous surfaces (including modified porous surfaces prepared according to the methods describe herein) of a medical implant, simultaneously, by using different cathodes and/or different electrolyte solutions for the smooth surfaces and the porous surfaces to thereby create separate electrolytic reactions at the smooth surface and porous surface, e.g., by providing separate containers or a divided container for holding separate electrolytes and/or cathodes. The amount of the bioactive agent or therapeutic agent deposited on the smooth surface and porous surface can be controlled in this system by also using a variable cathode method as described herein.

To further illustrate the methods, compositions and systems disclosed herein, a non-limiting list of aspects of the invention provided here:

Aspect 1 can include or use a method of modifying a porous surface of a medical device, the method comprising: providing an electrolytic cell including an electrolyte solution at a temperature of about 10° C., or less, wherein the medical device comprises an anode of the electrolytic cell; and applying a voltage to the electrolytic cell sufficient to cause micro-arc oxidation at the porous surface of the medical device to form a plurality of micro-pores in the porous surface of the medical device.

Aspect 2 can include or use, or can optionally be combined with the subject matter of Aspect 1 to optionally include or use, a method wherein the temperature of electrolyte solution is maintained at about 10° C. or less while applying the voltage.

Aspect 3 can include or use, or can optionally be combined with the subject matter of any one or a combination of Aspects 1 or 2 to optionally include or use, a method wherein the electrolyte solution comprises a glycol, an emulsifier, a dispersant, a surfactant, or a combination thereof.

Aspect 4 can include or use, or can optionally be combined with the subject matter of any one or a combination of Aspects 1 through 3 to optionally include or use, a method further comprising vigorously agitating the electrolyte solution while the applying the voltage.

Aspect 5 can include or use, or can optionally be combined with the subject matter of any one or a combination of Aspects 1 through 4 to optionally include or use, a method wherein the voltage is applied as a rectified sine waveform.

Aspect 6 can include or use, or can optionally be combined with the subject matter of any one or a combination of Aspects 1 through 5 to optionally include or use, a method wherein the voltage is pulsed at a frequency between 10 Hz and 150 Hz.

Aspect 7 can include or use, or can optionally be combined with the subject matter of any one or a combination of Aspects 1 through 6 to optionally include or use, a method wherein the voltage is pulsed for a period between 1 millisecond and to 50 milliseconds.

Aspect 8 can include or use, or can optionally be combined with the subject matter of any one or a combination of Aspects 1 through 7 to optionally include or use, a method wherein the voltage comprises a peak voltage between 100 volts and 1000 volts.

Aspect 9 can include or use, or can optionally be combined with the subject matter of any one or a combination of Aspects 1 through 8 to optionally include or use, a method further comprising applying an ultrasonic wave to the electrolyte solution while applying the voltage.

Aspect 10 can include or use, or can optionally be combined with the subject matter of any one or a combination of Aspects 1 through 9 to optionally, include or use, a method wherein at least a portion of the medical device is masked with a material configured to resist degradation of the medical device by the electrolyte solution, a high electrolyte solution temperature, a high voltage or a high current, or to prevent anodization of the masked portion of the medical device.

Aspect 11 can include or use, or can optionally be combined with the subject matter of any one or a combination of Aspects 1 through 10 to optionally include or use, a method further comprising applying a metal composition to the porous surface of the medical device before immersing the porous surface of the medical device in the electrolyte solution.

Aspect 12 can include or use, or can optionally be combined with the subject matter of any one or a combination of Aspects 1 through 11, to optionally include or use, a method of manufacturing a plurality of metallic substrates, comprising: securing an electrode to each one of a plurality of metallic substrates in an electrolyte solution having a temperature of about 10° C. or less; providing a cathode in the electrolyte solution; and sequentially applying a voltage to each one of the plurality of metallic substrates, wherein sequentially applying the voltage includes using a controller to control the voltage and the timing of application of the voltage to each one of the plurality of metal substrates.

Aspect 13 can include or use, or can optionally be combined with the subject matter of any one or a combination of Aspects 1 through 12 to optionally include or use, a controller comprising a switch, a circuit board, a relay, or a combination thereof.

Aspect 14 can include or use, or can optionally be combined with the subject matter of any one or a combination of Aspects 1 through 13 to optionally include or use, a method further comprising circulating the electrolyte solution through a temperature regulating device to maintain the temperature of the electrolyte solution while applying the voltage.

Aspect 15 can include or use, or can optionally be combined with the subject matter of any one or a combination of Aspects 1 through 14 to optionally include or use, a method of depositing a therapeutic agent on a medical device having a smooth surface and a porous surface, the method comprising: providing an electrolytic cell to produce an electrolytic reaction, the electrolytic cell comprising a container holding an electrolyte solution and the therapeutic agent, a cathode, and an anode comprising the medical device; applying a voltage to the electrolytic cell; and manipulating the voltage to the cathode during the electrolytic reaction or manipulating a current created during the electrolytic reaction to control the deposit of the therapeutic agent on at least one of the smooth surface and the porous surface of the medical device.

Aspect 16 can include or use, or can optionally be combined with the subject matter of any one or a combination of Aspects 1 through 15 to optionally include or use, a method wherein the current is manipulated by decreasing or increasing the surface area of the cathode that is exposed to the electrolyte solution during the reaction.

Aspect 17 can include or use, or can optionally be combined with the subject matter of any one or a combination of Aspects 1 through 16 to optionally include or use, a method wherein manipulating the voltage includes switching the cathode on and off at least twice during the electrolytic reaction.

Aspect 18 can include or use, or can optionally be combined with the subject matter of any one or a combination of Aspects 1 through 17 to optionally include or use, a method wherein the container comprises a first compartment and a second compartment, the cathode comprises a first cathode disposed in the first compartment and a second cathode disposed in the second compartment, and wherein applying the voltage comprises applying a first voltage to the first cathode and applying a second voltage to the second cathode, the second voltage being different from the first voltage.

Aspect 19 can include or use, or can optionally be combined with the subject matter of any one or a combination of Aspects 1 through 18 to optionally include or use, a method wherein the electrolyte solution comprises a first electrolyte solution in the first compartment and a second electrolyte solution in the second compartment, the second electrolyte solution being different from the first electrolyte solution.

Aspect 20 can include or use, or can optionally be combined with the subject matter of any one or a combination of Aspects 1 through 19 to optionally include or use, a method further comprising circulating the first electrolyte solution, the second electrolyte solution, or both, through a temperature regulating device configured to maintain a temperature of the first electrolyte solution, the second electrolyte solution, or both.

Aspect 21 can include or use, or can optionally be combined with the subject matter of any one or a combination of Aspects 1 through 20, to optionally include or use an electrolytic cell for processing a medical device comprising a smooth surface and a porous surface, the electrolytic cell comprising: a first container configured to receive the smooth surface of the device, the first container comprising a first electrolyte solution and a first cathode; a second container configured to receive the porous surface of the medical device, the second container comprising a second electrolyte solution and a second cathode; and temperature regulating device configured to maintain a temperature of the first electrolyte solution, the second electrolyte solution, or both.

Aspect 22 can include or use, or can optionally be combined with the subject matter of any one or a combination of Aspects 1 through 21, to optionally include or use a system for anodizing a porous surface of a medical device, comprising: a container configured to retain an electrolyte solution; a temperature regulating device fluidly connected to the container and configured to heat or chill a solution being circulated therethrough; and a mixer coupled to the temperature regulating device and configured to agitate a solution returning to the container from the temperature regulating device.

Aspect 23 can include or use, or can optionally be combined with the subject matter of any one or a combination of Aspects 1 through 22, to optionally include or use a system further comprising an ultrasound transducer configured to be at least partially immersed in a solution and to transmit an ultrasonic wave therethrough.

Aspect 24 can include or use, or can optionally be combined with the subject matter of any one or a combination of Aspects 1 through 23, to optionally include or use a controller coupled to a power supply and to an anode, or a cathode, or both, to control application of a voltage.

Aspect 25 can include or use, or can optionally be combined with any portion or combination of any portions of any one or more of Aspects 1 through 24 to include or use, subject matter that can include means for performing any one or more of the functions of Aspects 1 through 24, or a machine-readable medium including instructions that, when performed by a machine, cause the machine to perform any one or more of the functions of Aspects 1 through 24.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure. Corresponding reference numerals indicate corresponding parts throughout the several views of the drawings.

Figure 5A:
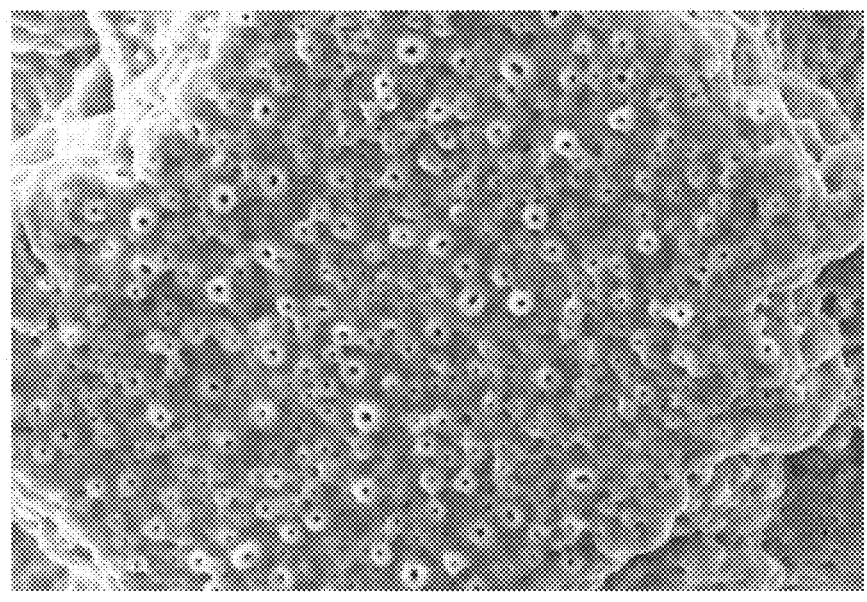
Figure 5B:
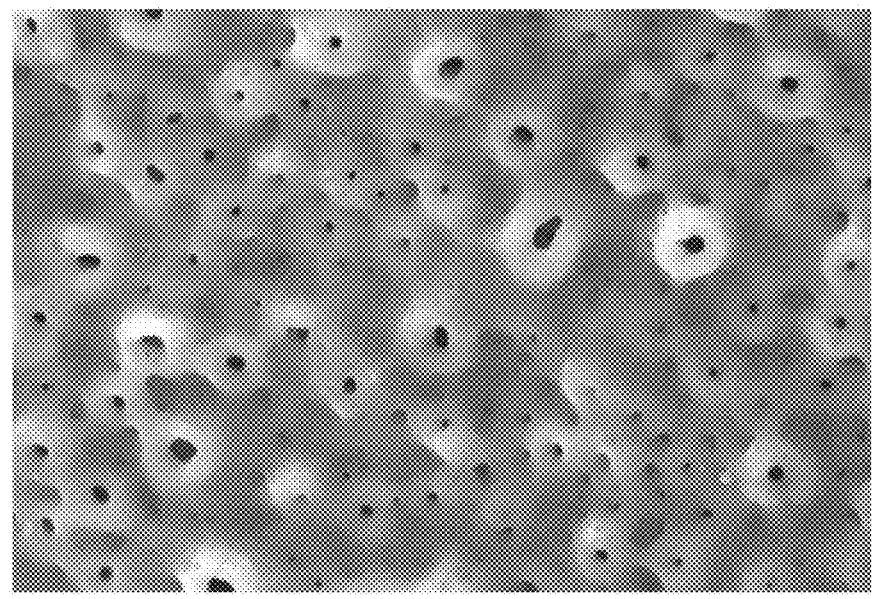

FIGS. 5A and 5B are scanning electron micrographs showing micro-pores of the modified porous surface of a medical device after modified micro-arc oxidation processing according to an example of the present patent disclosure. In FIG. 5A, processing was performed in an acid electrolyte solution at a temperature of 1-2° C.; a titanium dioxide composition was applied to at least partially fill the macropores of the implant porous surface before immersion in an electrolyte solution, and an applied voltage of 200V AC, rectified sine wave was used. In FIG. 5B processing was performed in an acid electrolyte solution at a temperature of 0° C.-10° C.; ultrasonic waves were applied together with a voltage of 200 V AC, rectified sine waveform.

Figure 6:
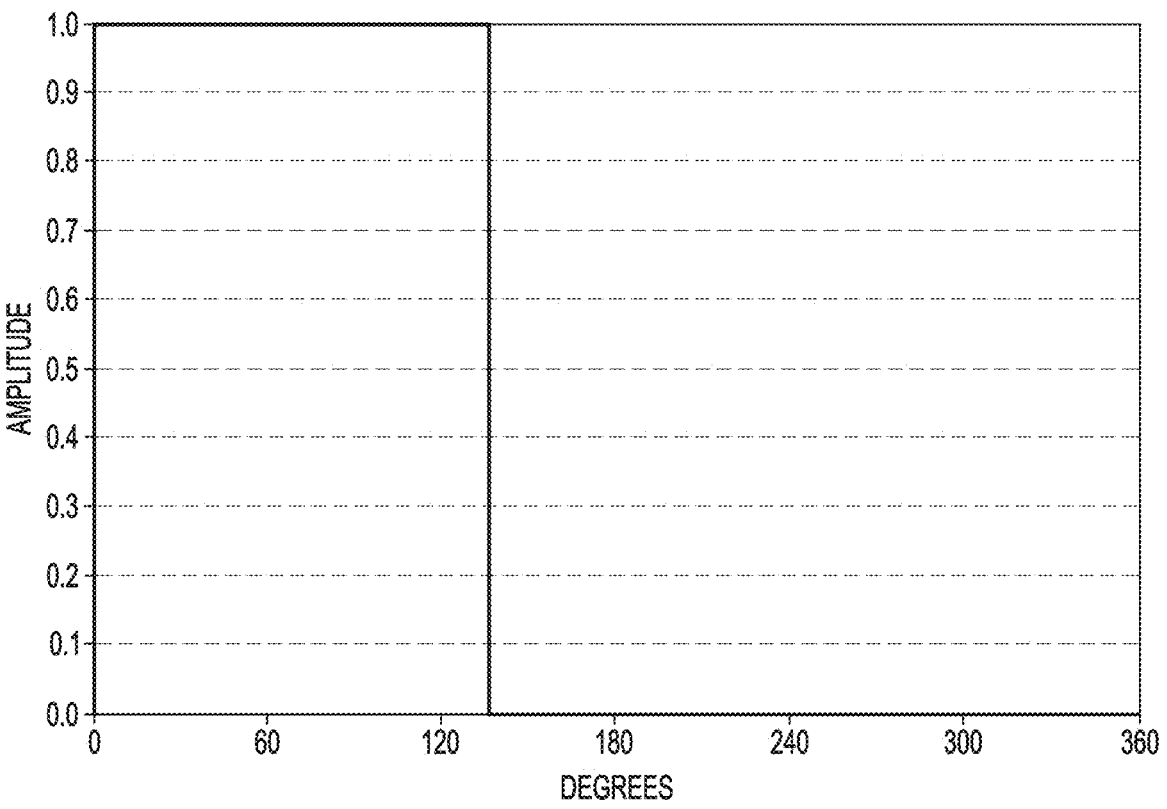

FIG. 6 is a graph showing an example of a waveform that can be used in a modified micro-arc oxidation process according to one or more examples of the present patent disclosure.

Figure 7:
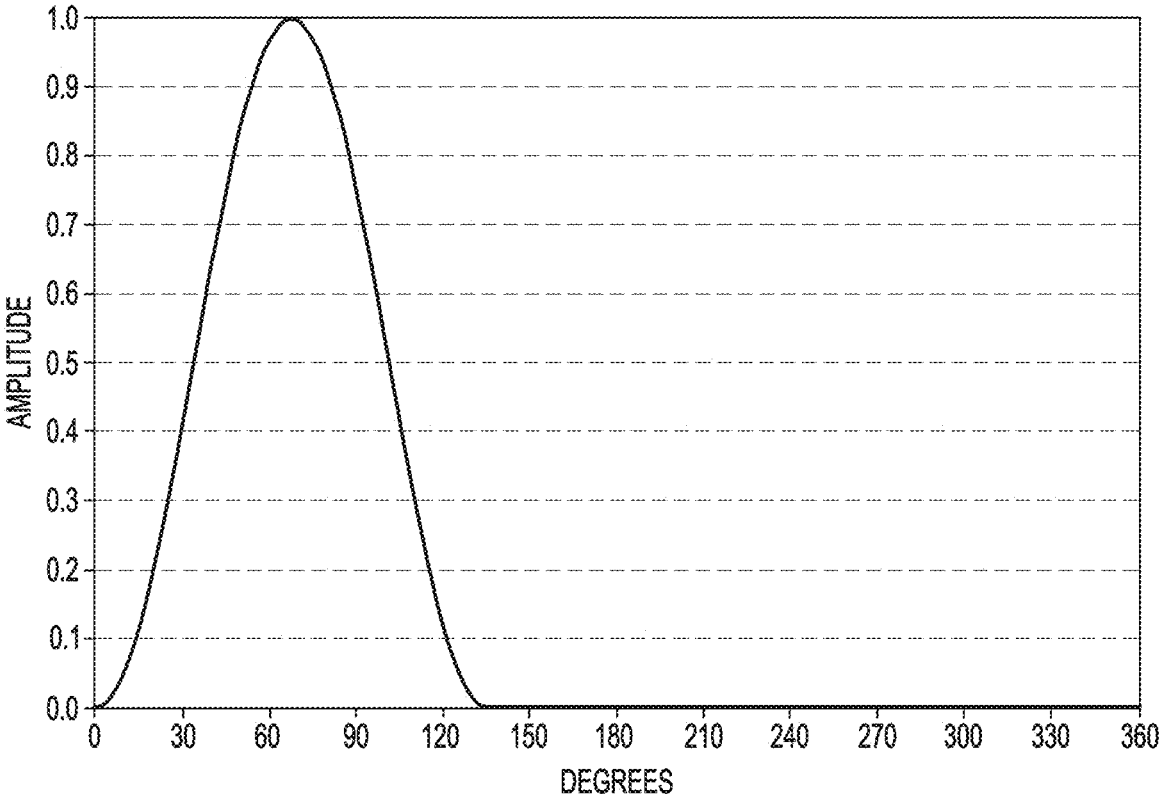

FIG. 7 is a graph showing another example of a waveform that can be used in a modified micro-arc oxidation process according to one or more examples of the present patent disclosure.

Figure 8:
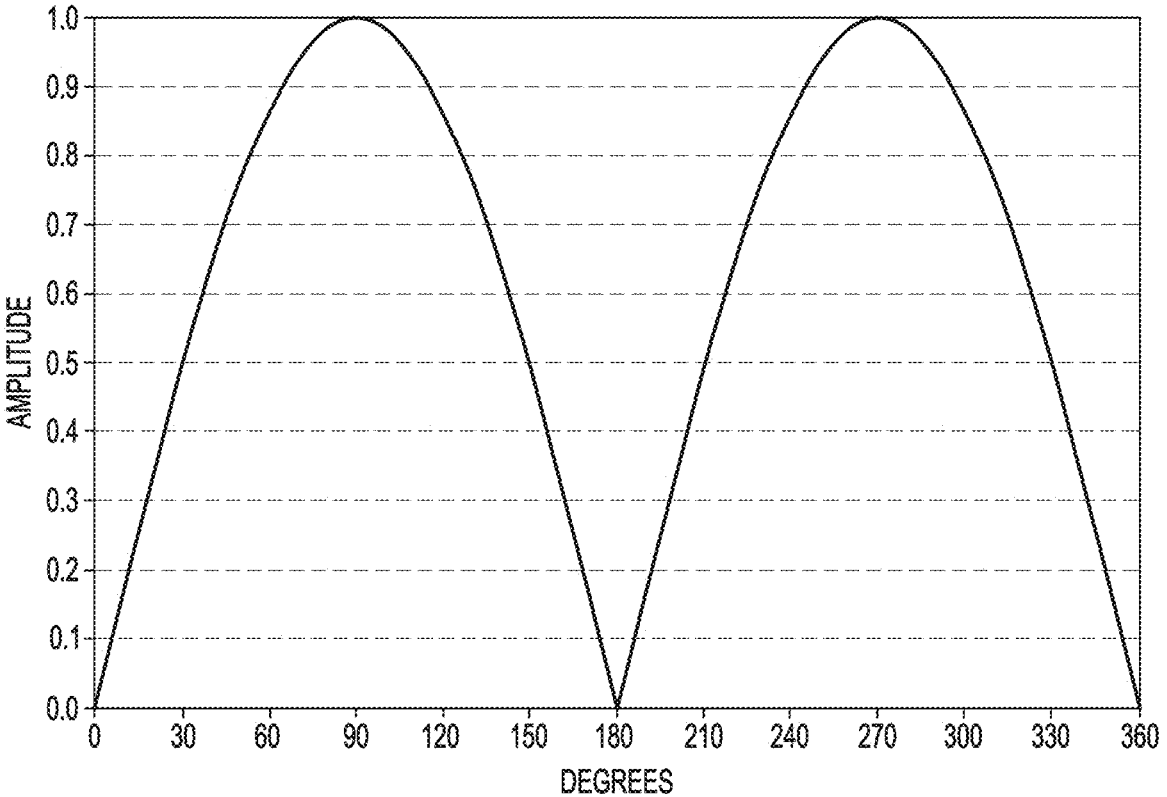

FIG. 8 is a graph showing yet another example of a waveform that can be used in a modified micro-arc oxidation process according to one or more examples of the present patent disclosure.

Figure 9A:
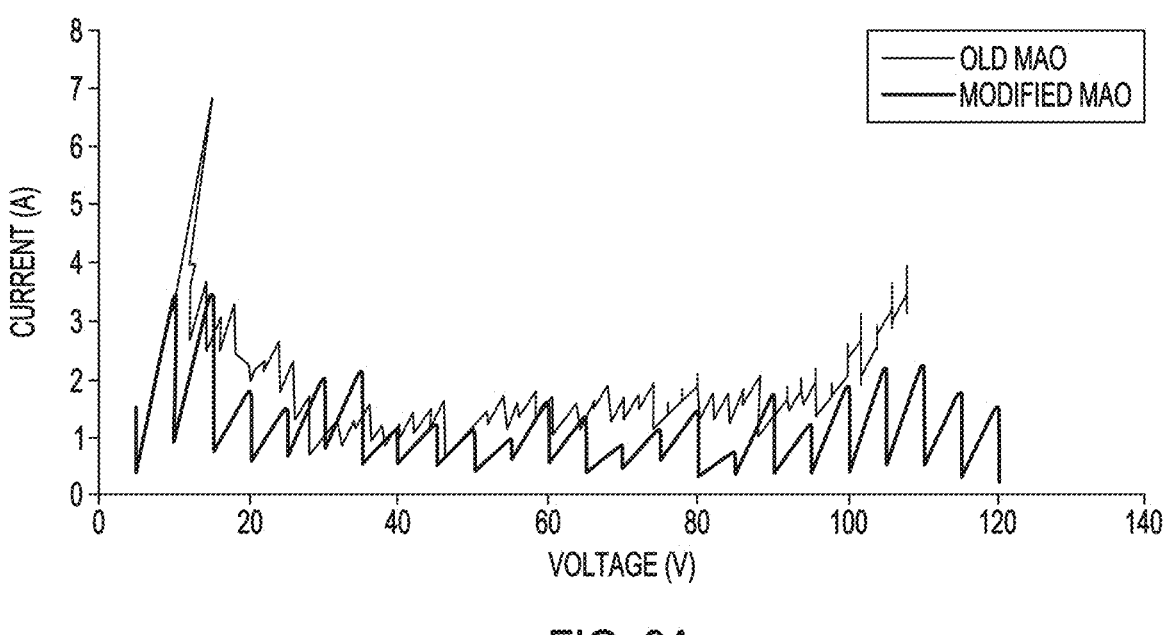
Figure 9B:
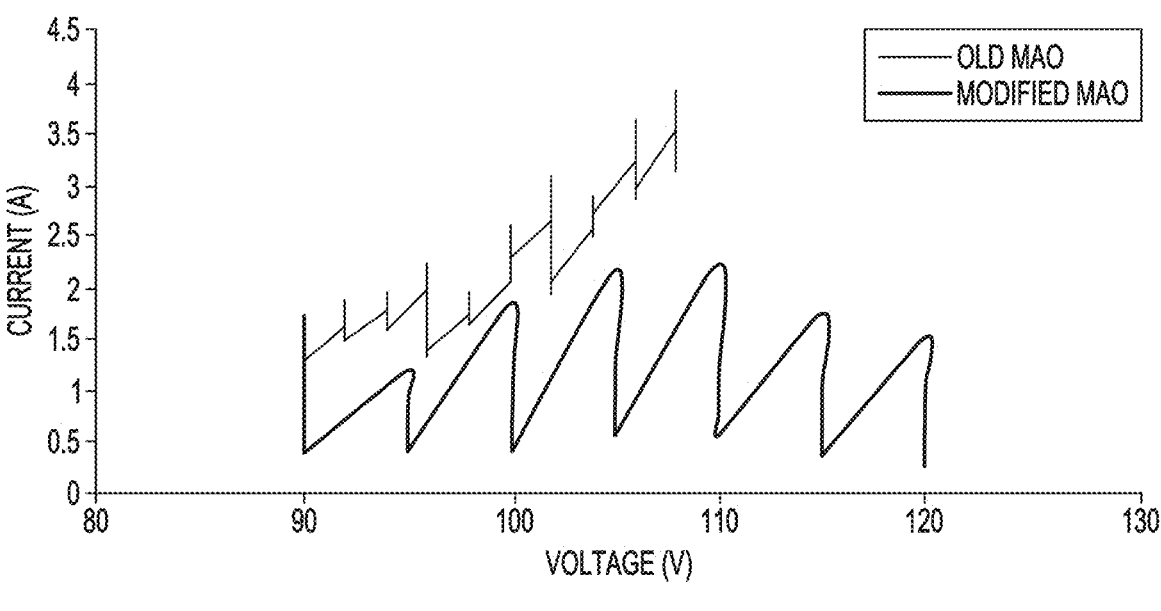

FIGS. 9A and 9B are graphs showing the changes in current resulting from an applied voltage using standard micro-arc oxidation processing of a porous metallic substrate and using a modified micro-arc oxidation processing of a porous metallic substrate according to one or more examples of the present patent disclosure.

Figure 10:
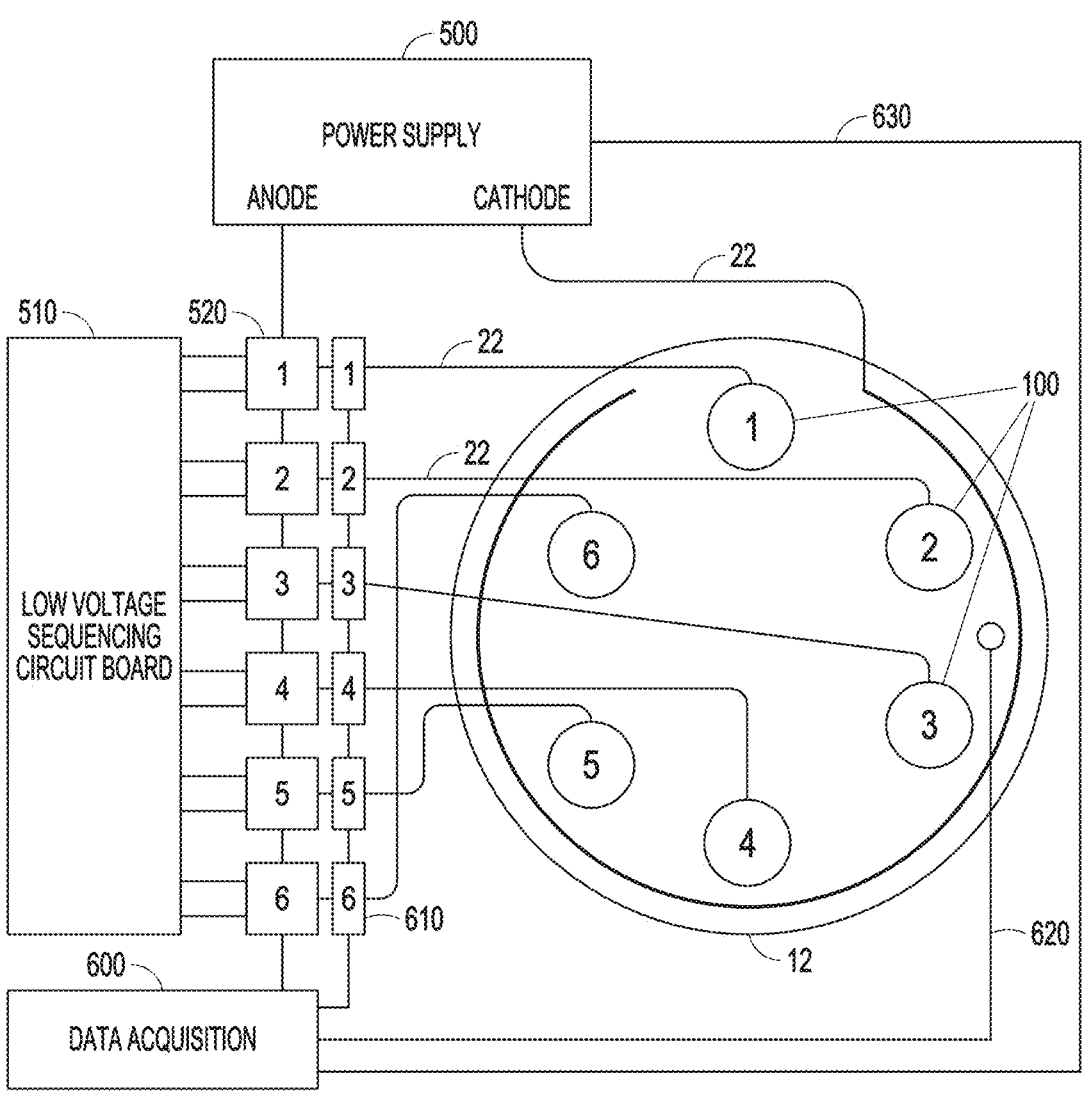

FIG. 10 illustrates a diagram of a system for processing a plurality of medical devices in a single electrolytic cell using a modified micro-arc oxidation process according to one or more examples of the present patent disclosure.

Figure 11:
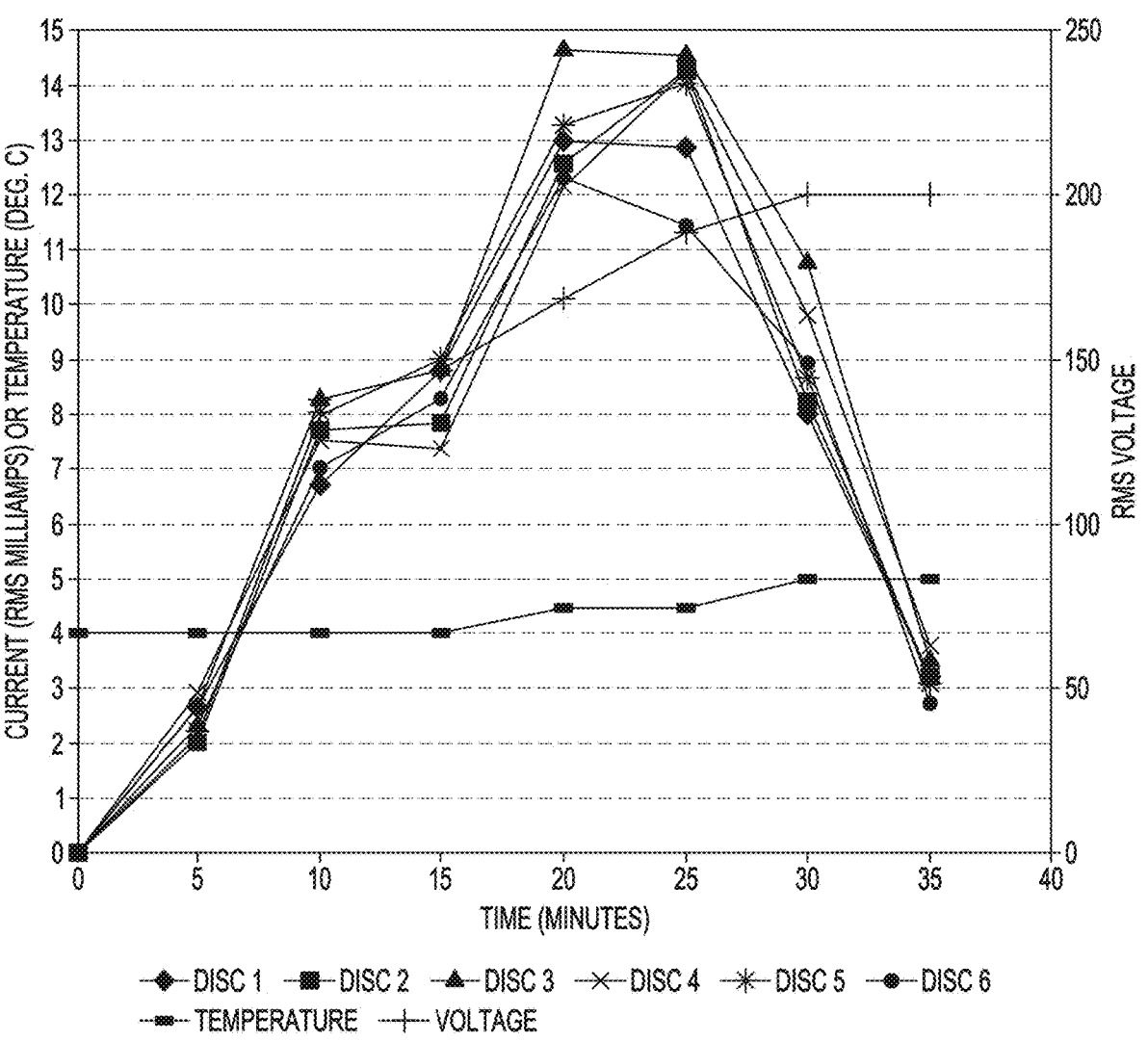

FIG. 11 is a graph of data acquired during processing of a plurality of medical devices according to FIG. 10, using a modified micro-arc oxidation process according to one or more examples of the present patent disclosure.

Figure 12A:
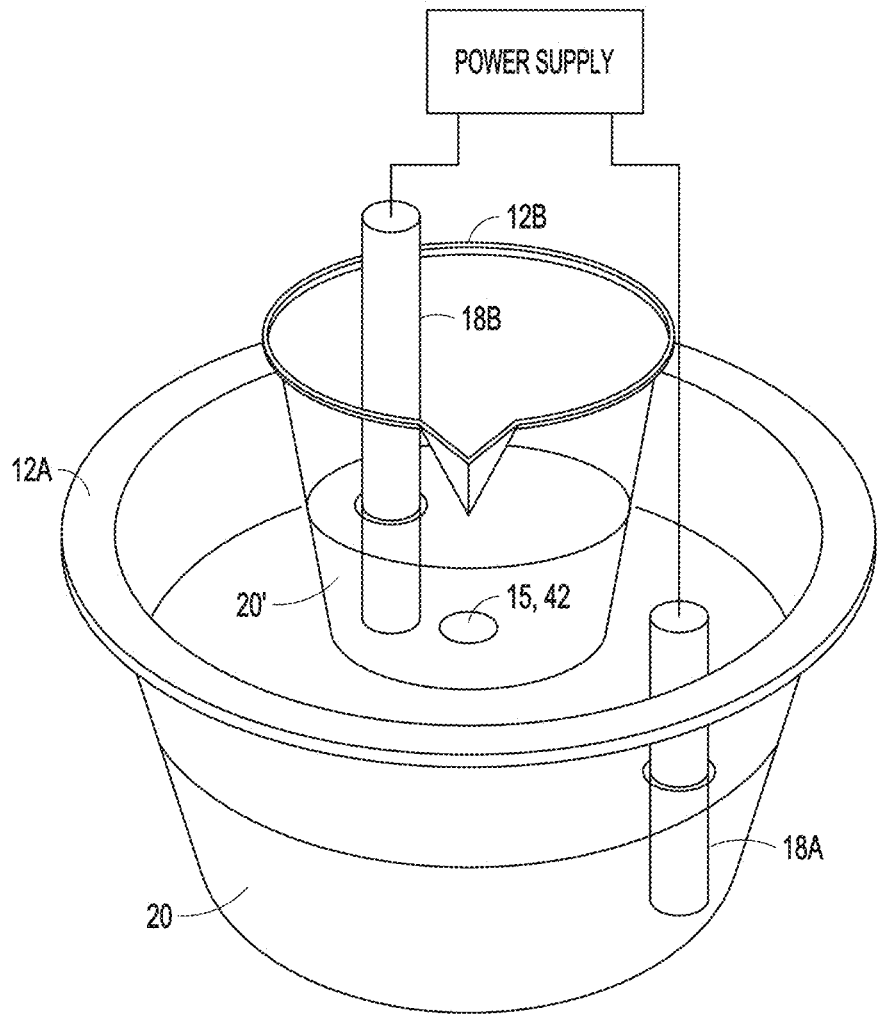
Figure 12B:
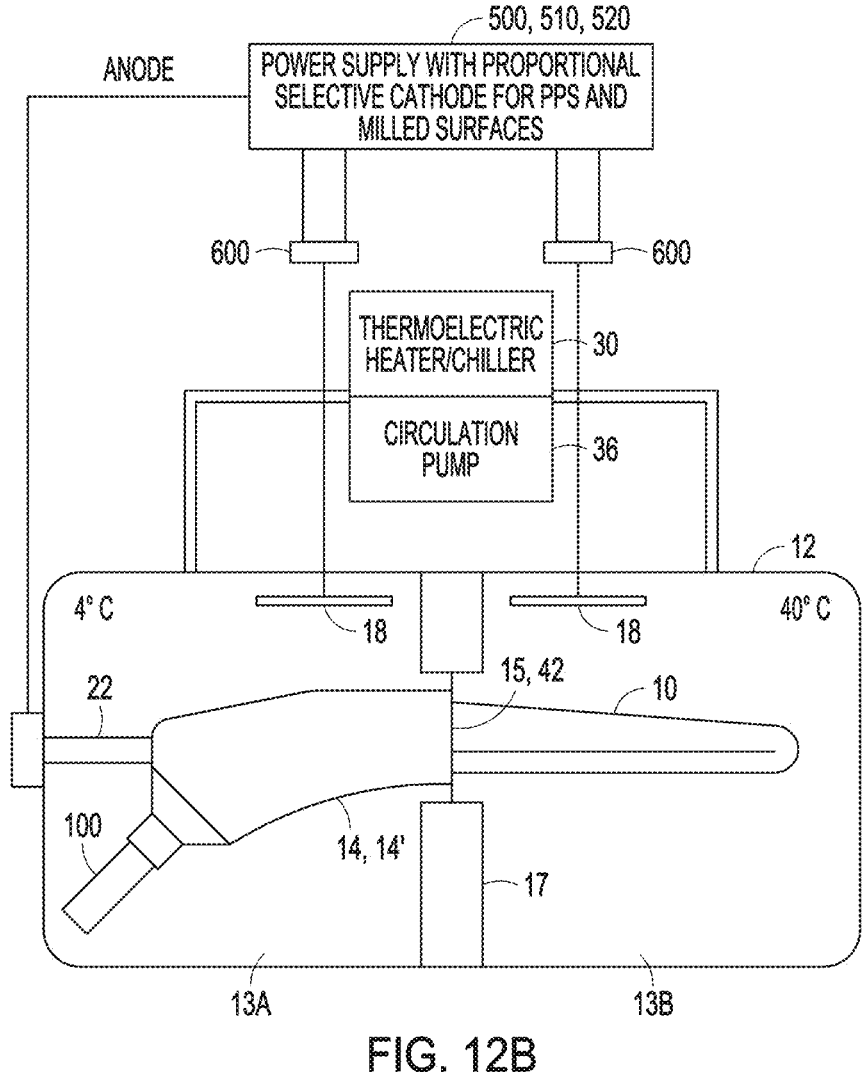
Figure 12C:
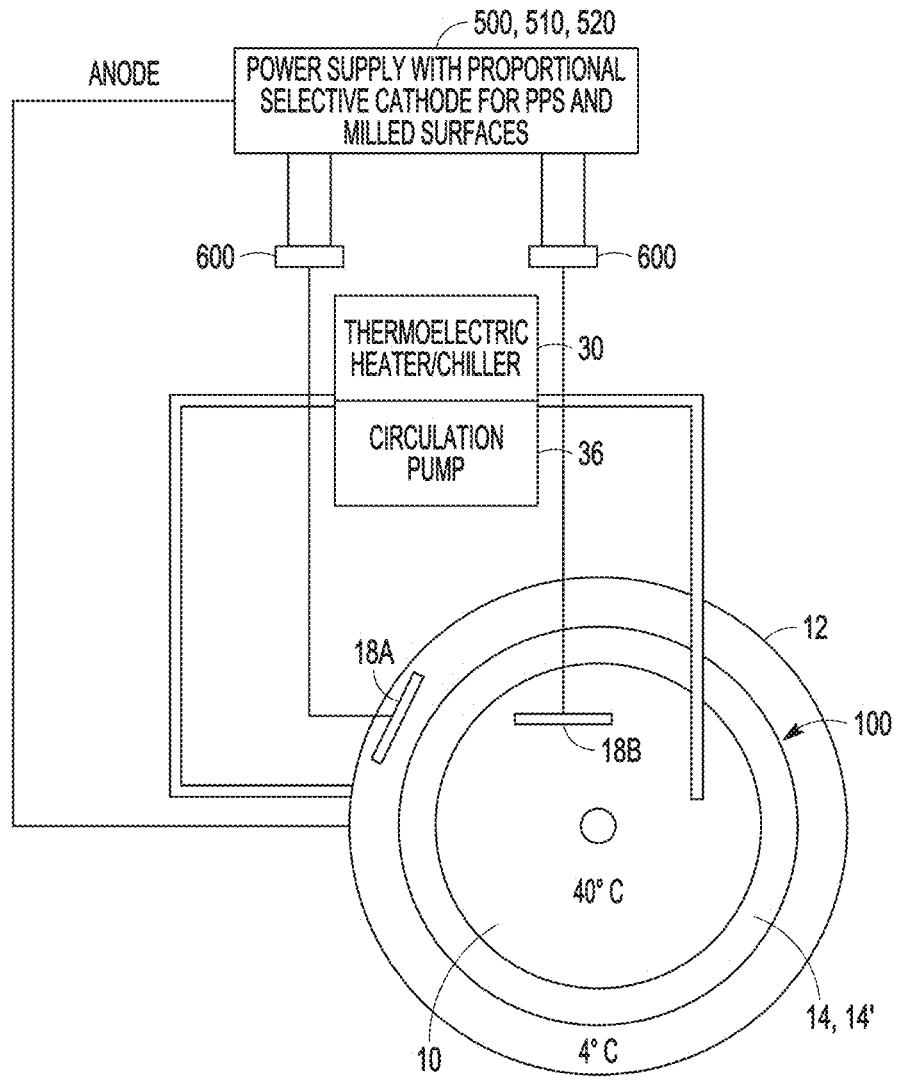

FIGS. 12A, 12B and 12C illustrate systems for depositing a therapeutic on a medical implant according to one or more examples of the present patent disclosure.

Figure 13A:
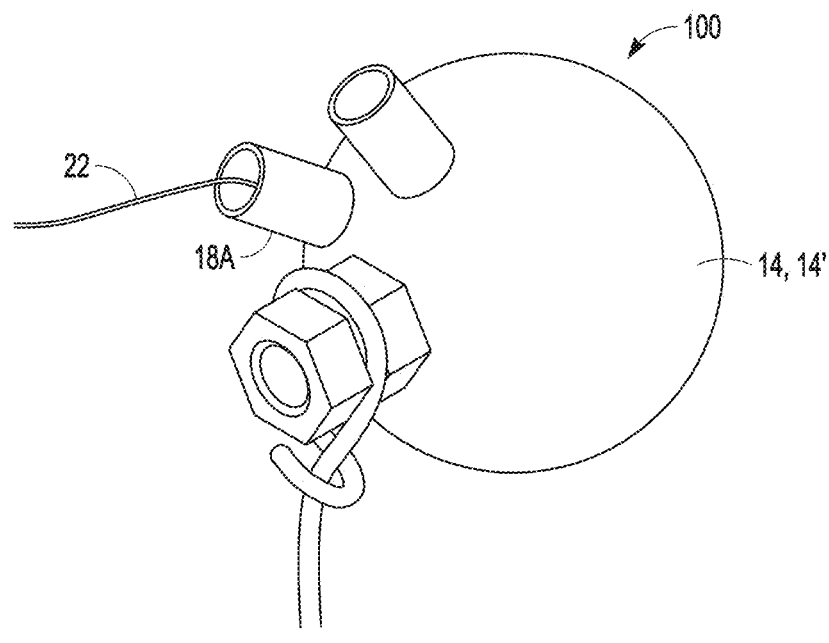
Figure 13B:
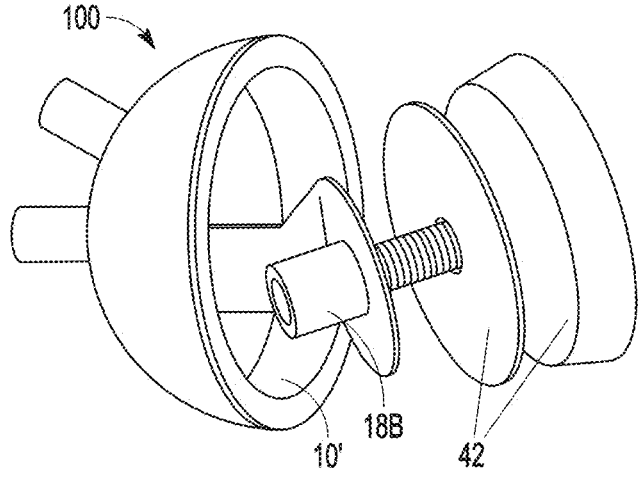

FIGS. 13A and 13B illustrate a medical device having both porous surfaces and smooth surfaces which can processed to receive a deposit of therapeutic agent according to the system and method shown in FIG. 12C.

Figure 14:
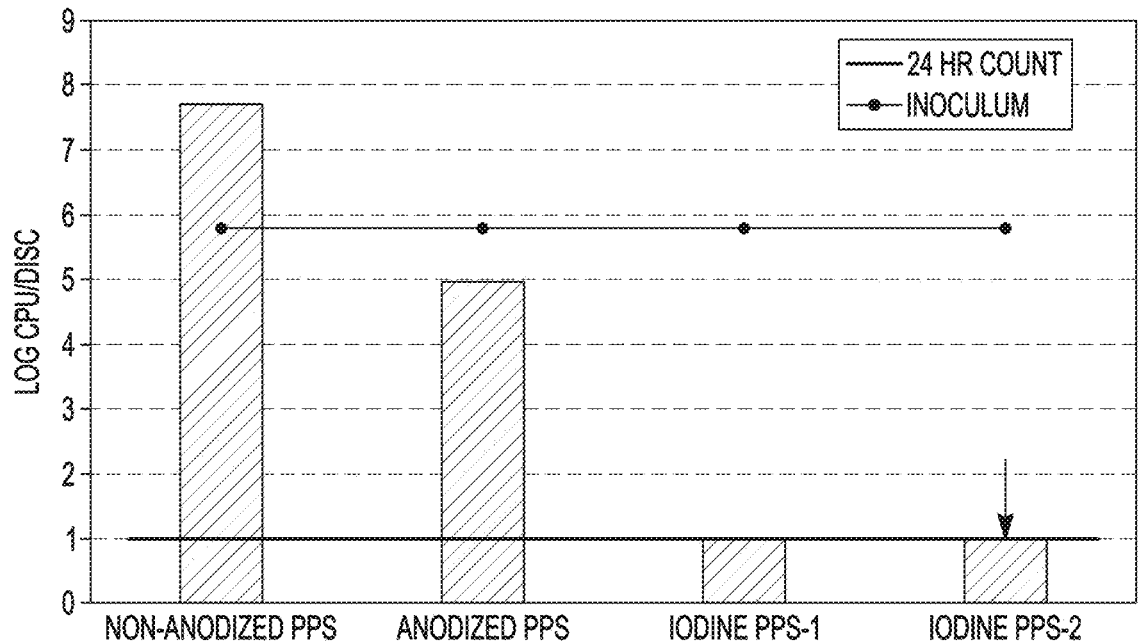

FIG. 14 is graph showing the bacterial growth on medical devices (i) treated by a modified micro-arc oxidation process according to one or more examples of the present patent disclosure and (ii) on which an antimicrobial therapeutic agent has been deposited according to one or more examples of the present patent disclosure (PPS-1is a smooth surface coated with antimicrobial agent; PPS-2 is a modified porous surface comprising micro-pores coated with antimicrobial agent).

DETAILED DESCRIPTION

Examples of the methods will now be described more fully with reference to the accompanying FIGS.

The present technology generally provides methods for modifying a porous surface or porous coating, including a roughened surface or a rough coating, of an implantable medical device (collectively, referred to of herein as a "porous surface"). In one example the implantable medical device comprises a substrate that is metallic. In another example the implantable medical device comprises a substrate that is formed of a substance that is not metallic, but the medical device includes a porous surface that is metallic. As used herein, "metallic" means a substance comprising any metal element or any combination of metal elements e.g., an alloy or a ceramic. In certain examples, the medical device and/or the porous surface of the implantable medical device can comprise ceramics, aluminum, stainless steels, titanium, titanium alloys Ti6Al4V, Ti6Al7Nb), vanadium, zirconium, hafnium, niobium, molybdenum, magnesium, tantalum, tungsten, chromium, cobalt, Co—Cr alloys, sodium, potassium, iron, calcium, copper, silver, gold, or any other known metal or metal alloy, e.g., alloys of nickel, niobium, cobalt, molybdenum, and chromium.

An implantable medical device suitable for use in the methods described herein can comprise a porous surface. A porous surface can be formed by application of a biologically active or biocompatible material, such as hydroxyapatite or other calcium phosphate compound, e.g., using known plasma-spray techniques. In another example, a porous surface can be formed on the medical device by plasma-spraying a substance, e.g., titanium powder, on the implant surface or by sintering a material onto the implant surface, e.g., beads made of titanium or titanium alloy. In yet another example, pores can be formed in the medical device by machining or cutting the surface of the implant, sandblasting, or by a chemical treatment, e.g, acid etching. In other examples, a porous surface can be an oxidized metal coating (e.g., by formed by anodic oxidation, see U.S. Pat. No. 5,478,237) formed on the surface of the implant. In a preferred example, porous coating can be applied to create a structural architecture on the implant surface that mimics the structural architecture of cancellous bone. The rough or porous coating on a medical implant can be formed by any one or any combination of known methods, including plasma spray (e.g., Porous Plasma Spray™, Biomet; Orthopedic TPS Coating, ORCHID; Bio-Coat Dental TPS Coating, ORCHID), additive manufacturing or 3D printing (e.g., OsseoTi™, Biomet), chemical vapor deposition (e.g., Trabecular Metal™, Zimmer), physical vapor deposition, chemical etching, electrochemical methods, sublimation of pore formers (Regenerex™, Biomet), dissolution of pore formers (CSTi™, Zimmer), or pressing metallic fibers (e.g., a metallic mesh) or welding of metallic fibers (e.g., fiber metal pads) or sintering of metallic beads onto the surface of the implant. Any porous metallic medical implant or other medical device can be modified according to the methods described herein. In one example, the metallic comprises titanium or a titanium alloy.

The porous surface of the medical device includes surfaces that define the pores of the porous surface. The surfaces that define the pores of the porous surface are referred to herein as "pore-forming surfaces," The pores defined by the pore-forming surfaces are referred to herein as "macro-pores." The term "macro-pores" should not be understood to mean pores of any particular size or shape, and the macro-pores can be of any size and can have any shape.

Figure 1A:
FIGS. 1A and 1B are scanning electron micrographs showing a porous metallic substrate after processing using an example of standard micro-arc oxidation in an acid electrolyte bath at room temperature.
Figure 1B:
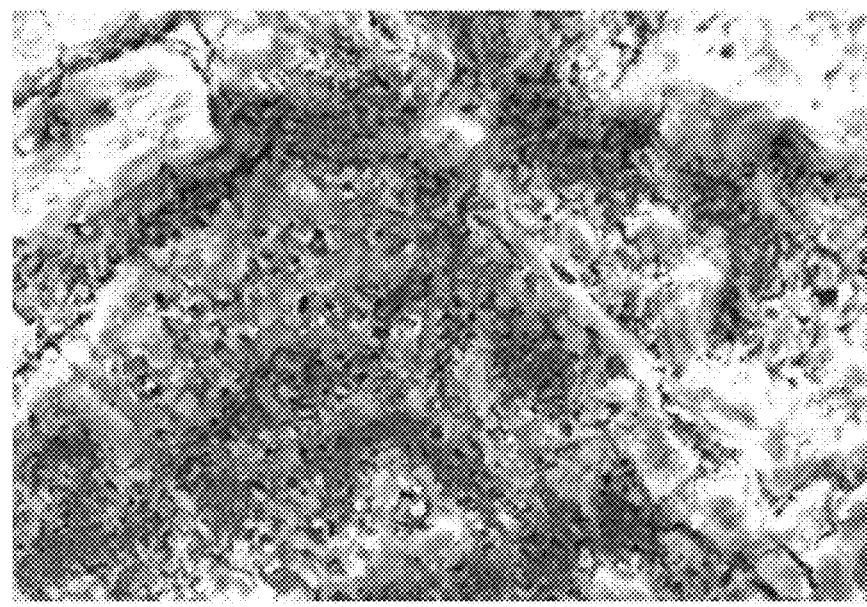
Figure 2:
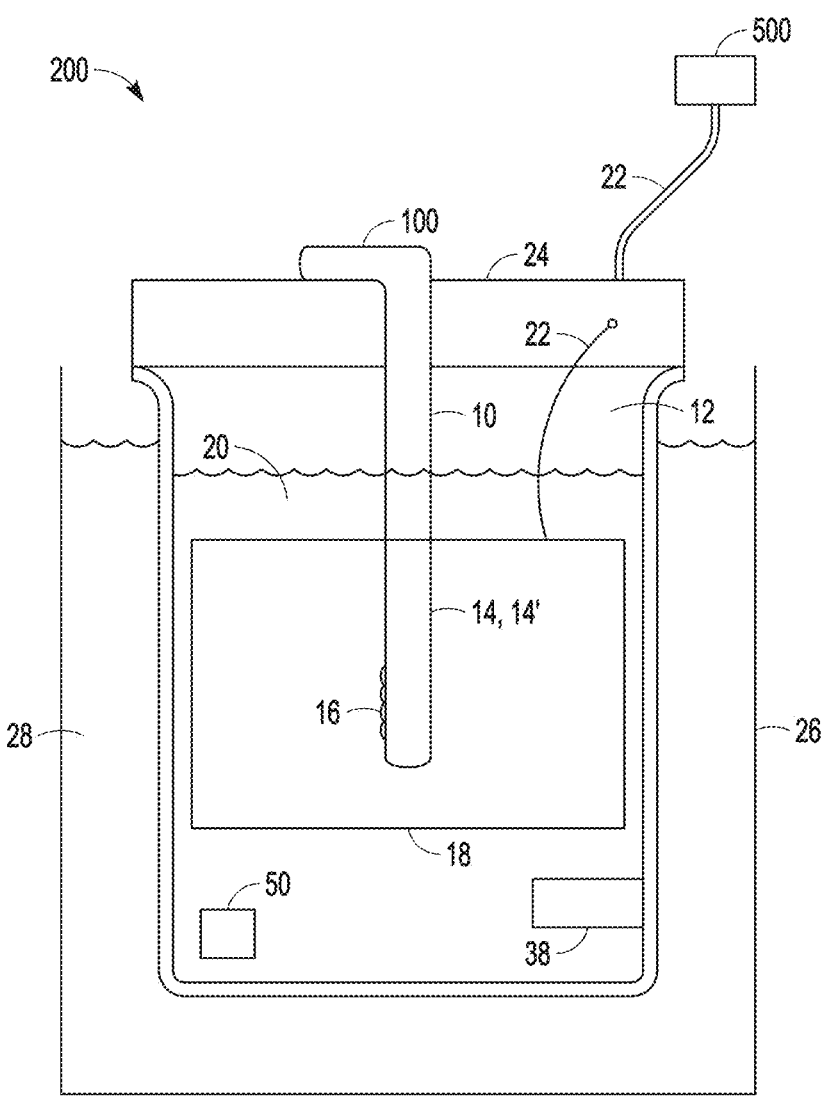
FIG. 2 is a side view of a system for carrying out a modified micro-arc oxidation process according to one or more examples of the present patent disclosure.
Figure 3:
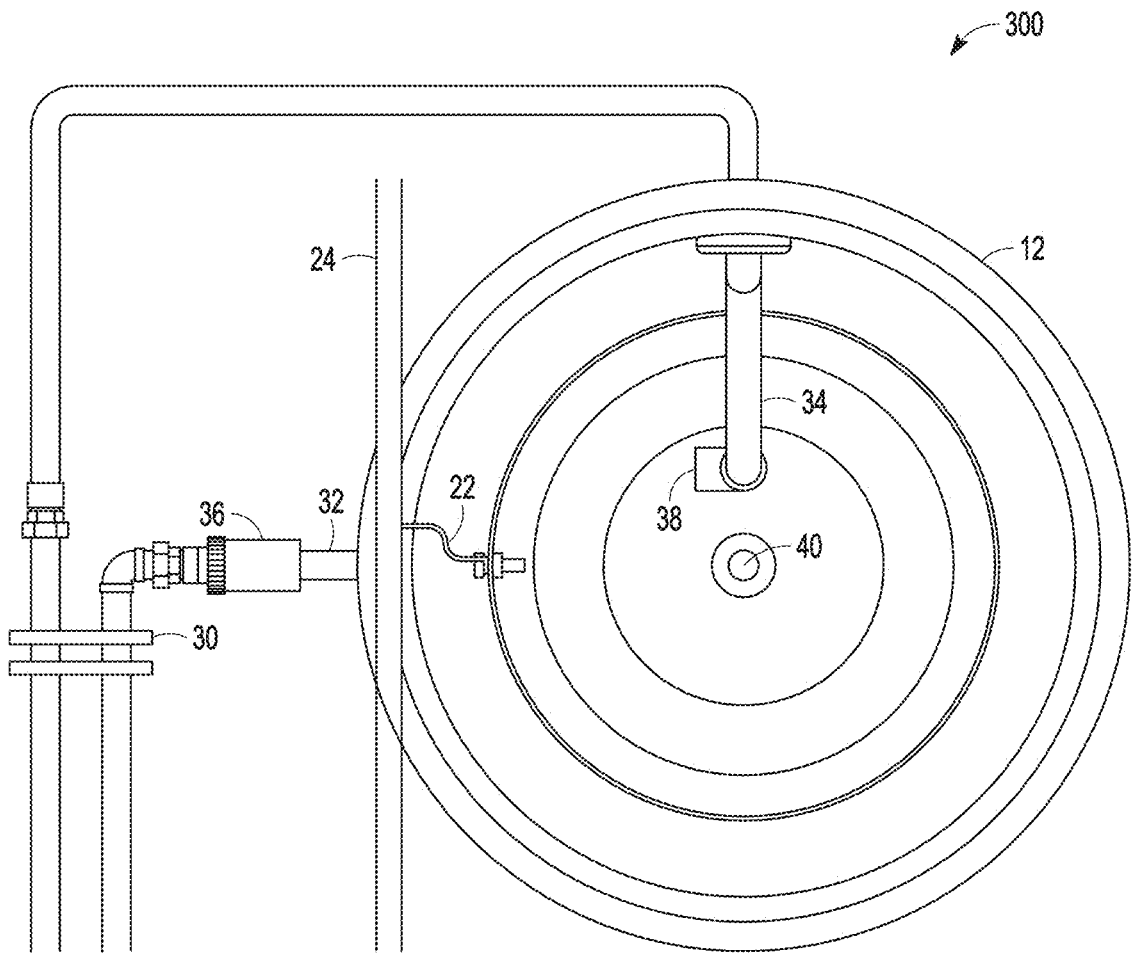
FIG. 3 is a top view of a system for carrying out a modified micro-arc oxidation process according to one or more examples of the present patent disclosure.
Figure 4:
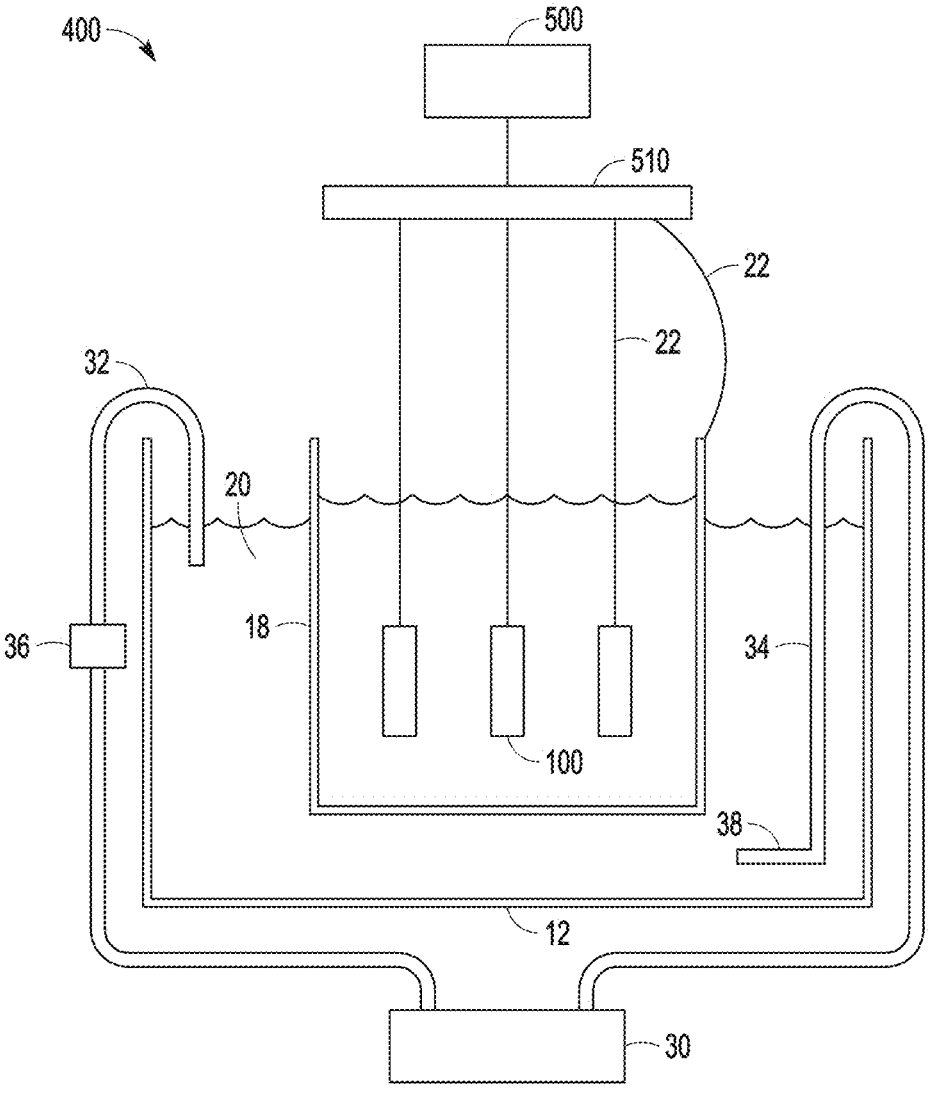
FIG. 4 is a side view of a system for carrying out a modified micro-arc oxidation process according to one or more examples of the present patent disclosure.

As shown in FIGS. 2, 3 and 4, the present technology provides a system (200, 300, 400) for modifying a porous surface of an implantable medical device (100) by subjecting the medical device to modified micro-arc oxidation processing as described in detail below. The modified micro-arc oxidation system (200, 300, 400) can include a container (12) configured to hold a medical device (100) having a porous coating or porous surface (14), and a cathode (18). In an example, the medical device can also include one or more non-porous surfaces (10), which can comprise smooth surfaces or milled surfaces (collectively, non-porous surfaces are referred to herein as "smooth surfaces"). In one example, the cathode (18) can comprise one or more walls (19) of the container (12). In another example, the cathode (18) can comprise a piece of metal separate from the container (12). In one example, the cathode can be of a size, a shape, or both, to substantially mimic or conform to a size, a shape, or both, of the container (12). In an example, the container (12) can be configured to hold a volume of an acidic or alkaline electrolyte solution (20) sufficient to cover the porous coating or porous surface (14) of the medical device (100). In certain examples, the system (200, 300, 400) can include a removable ultrasound transducer (50) configured to be immersed in an electrolyte solution (20). The medical device (100), which serves as the anode, and the cathode (18) are each configured to be coupled by a coupling (22) to an electrical power source (500). In one example, the medical device (100), the cathode (18), or both, can be mounted on or electrically coupled to a holder or bus bar (24). In another example, the medical device (100), the cathode (18), or both, can mounted on or electrically coupled by a coupling (22) to a bus bar (24) and the bus bar (24) can be electrically coupled by a coupling (22) to an electrical power source (500).

The modified micro-arc oxidation system (200, 300, 400) can be configured with a means to heat, cool or maintain a desired temperature of the electrolyte solution (20) during processing. In one example, the system (200) can include a cooling tank (26) configured to hold a cooling solution (28), e.g., water, antifreeze, or other coolant. The cooling tank (26) can be configured to hold the container (12) at least partially immersed in a cooling solution (28) during micro-arc oxidation processing of the medical device (100). In another example, the modified micro-arc oxidation system (300, 400) can comprise one or more devices to heat or chill a fluid, e.g., a thermoelectric heater, a thermoelectric chiller, or a thermoelectric heater/chiller (such devices are sometimes collectively referred to herein as "heat exchangers") (30) to cool or maintain a desired temperature of the electrolyte solution (20), the cooling solution (28), or both. To maintain a desired temperature of a cooling solution (28), an electrolyte solution (20), or both, e.g., at about 10° C. or below 10° C., during modified micro-arc oxidation processing, the solution (20, 28) can be withdrawn from the container (12) through a first pipe (32), circulated through a heat exchanger (30), and can be passed from the heat exchanger (30) through a second pipe (34) and reintroduced into the container (12). The operation of the heat exchanger (30) can be controlled automatically to maintain the desired temperature of the electrolyte solution (20). In one example, the system (300, 400) can comprise a pump (36) disposed between the first pipe (32) and the heat exchanger (30) and configured to withdraw the solution (20, 28) from the container (12) and into the first pipe (32). In a preferred example, the heat exchanger (30) can be a plate heat exchanger. In another example, the first pipe (32) can be disposed in a lower portion of the container (12). In another example the first pipe (32) can be a connected to a bore (40) formed in a lower portion of the container (12), e.g., a lower wall or bottom wall (19) of the container (12).

In still another example the modified micro-arc oxidation system (200, 300, 400) can be configured with an agitator (38) to create vigorous agitation in the electrolyte solution (20). In one example, the agitator can comprise a means to mechanically stir the electrolyte solution, e.g., a magnetic stirrer. In another example, the agitator (38) can comprise a feature disposed adjacent to the second pipe (34), configured to cause turbulence or to create a vortex about the medical device (100) as the electrolyte solution (20) is passed through the second pipe (34) and into the container (12). In a preferred example, the agitator (38) can comprise a pipe coupling that creates vortex in the electrolyte solution (20). In certain examples, the pipe coupling (38) can comprise an angled pipe configured to circulate the electrolyte solution (20) entering from the second pipe (34) about the medical device (100). In another example, the system (200, 300, 400) can comprise an agitator (38) in the form of both a mechanical stirrer and a pipe coupling coupled to the second pipe (34).

Anodic oxidation is effected by applying an electrical voltage between a substrate, e.g., the medical device (100), and a cathode (18) while immersed in an electrolyte solution (20), such that the substrate is given a positive potential, and the difference in electrical potential between the substrate and cathode (18) gives rise to a current of negatively (positively) charged electrolyte ions to the substrate resulting in an oxide layer forming on the surface of the substrate. In a micro-arc oxidation process, the substrate, e.g. medical device (100), is subjected to a high voltage or electrical current density while it is submerged in an acid or alkaline electrolyte solution (20). Electrical discharges on the porous surface (14) of the substrate, e.g., medical device (100) form an adherent, micro-porous oxide coating (14').

In one example of a modified micro-arc oxidation processing, prior to micro-arc oxidation, a porous medical device (100) can optionally be cleaned, degreased, and/or polished. In an example of modified micro-arc oxidation processing, the porous surface (14) of the implantable medical device (100) can optionally be at least partially coated with a metal coating material (16) comprising at least one metal (e.g., a metal oxide or a ceramic). In one example, the porous surface (14) can be coated with a metal coating material (16) such that at least some of the macro-pores of the porous surface (14) are partially filled or filled, with the metal coating material (16). The metal coating material (16) can comprise any metal that is suitable for subsequent micro-arc oxidation at the porous surface of the medical device. For example, a metal coating material (16) can comprise any one or any combination of metals, ceramics and alloys, e.g., aluminum, stainless steels, titanium, vanadium, zirconium, hafnium, niobium, molybdenum, magnesium, tantalum, tungsten, chromium, cobalt, sodium, potassium, iron, calcium, copper, silver, gold, or any other known metal, alloy or ceramic. In one example, the metal of the metal coating material (16) can comprise one or more metal oxides. The metal of the metal coating material (16) can be in the form of a metal oxide powder, e.g., titanium dioxide powder. In a preferred example, the metal oxide can comprise titanium dioxide, in the form of rutile phase or anatase phase. In another example, a metal oxide powder of the metal coating material (16) can have a particle size ranging from one nanometer to ten microns. In some examples, the metal coating material (16) can comprise a mixture of a metal and a solvent, e.g., water or alcohol or organic solvent. In certain examples, the metal coating material can be in the form of a slurry or a paste. In another example, the mixture of the metal and solvent can further comprise about 1% to about 10%, by weight or by volume, of a glycol (e.g., ethylene glycol or polyethylene glycol), an emulsifier, a dispersant, a surfactant, or a combination thereof. The metal coating material (16) can be applied to the porous surface (14) of the medical device (100) by any conventional method, such as immersion of the porous surface (14) of the medical device in the metal coating material, brushing the metal coating material on the porous surface of the medical device, spraying the metal coating material on the porous surface, or a combination thereof.

In one example in which the medical device (100) is coated with a metal coating material (16), application of the metal coating material (16) to the porous surface (14) of the medical device (100) can be facilitated by use of ultrasonic waves (0, a vacuum (V), or any other means that can drive the metal coating material (16) into the pores and crevices of the porous surface (14) of the medical device (100). In an example, ultrasonic waves (U) can optionally be applied to the implantable medical device (100) during application (e.g., by immersion, brushing or spraying) of the metal coating material (16). In another example, ultrasonic waves (U) can optionally be applied to the medical device (100) after the medical device (100) has been coated with the metal coating material (16), e.g., by immersion, brushing or spraying. In yet another example, the medical device (100) can be immersed in container comprising the metal coating material (16), e.g., titanium dioxide, and the container can be immersed in a bath in which ultrasonic waves (U) are produced, e.g., using an immersible ultrasonic transducer (50). In one example, application of the metal coating material (16) to the porous surface (14) of the medical device (100) can be optionally performed under vacuum (V). For example, the implantable medical device (100) can be immersed in container comprising the metal coating material (16) e.g., titanium dioxide, and the container can be placed in a vacuum chamber to provide a vacuum (V). After the porous surface (14) of the medical device (100) is coated with the optional metal coating material (16), the medical device can be air dried. In another example the coated medical device can be dried under heat, e.g., in an oven. In an example, the medical device (100) coated with the metal coating material (16) can be heated to a temperature of between 50° C. and 100° C. for an appropriate period, e.g., 15 minutes to 2 hours, to dry the optional metal coating material (16) that has been applied to at least a portion of the porous surface (14) of the medical device (100).

A medical device (100), including a medical device that has received an optional coating of a metal coating material (16) on a porous surface (14) of the medical device (100) as described above, can be submerged or immersed in an acidic or alkaline electrolyte solution (20). In certain examples, the entire medical device (100) can be submerged or immersed in an electrolyte solution (20). In other examples only the porous surface (14) of the implantable medical device can be submerged or immersed in the electrolyte solution (20), while other portions of the medical device (14) are not in contact with the electrolyte solution (20), e.g., a smooth surface (10) or a select portion of a porous surface (14) can be held outside of the electrolyte solution or otherwise protected from contact with the electrolyte solution. In one example, the porous surface (14) of the medical device that is immersed in the electrolyte solution (20) can comprise a dried, metal coating material (16) as described above.

Electrolyte solutions (20) that can be used in the modified micro-arc oxidation processes described herein can include any acidic or alkaline electrolyte solution or any combination of electrolytes suitable for oxidation of metal. In certain examples the electrolyte solution can be an acidic electrolytic solution, which can include a combination of electrolytes to form an acidic electrolyte solution. In other examples the electrolyte solution can be an alkali electrolytic solution, which can include a combination of electrolytes to form an alkaline electrolyte solution. One of ordinary skill in the art will understand that the electrolyte solution (20) selected should be one that is appropriate for the metal composition of the surface being anodized, e.g., the medical device, the porous surface of the medical device, and/or the metal coating material applied to the porous surface of the medical device. Examples of acidic electrolyte solutions (20) that can be used in any of the modified micro-arc oxidation methods used to modify a porous surface of an implantable medical device can include: an acid sulfuric acid-water mixture (e.g., content of sulfuric acid: 5 to 30 mass % and preferably 10 to 25 mass %); a sulfuric acid-phosphoric acid-water mixture (e.g., sulfuric acid 10 g/l to 50 or more, and phosphoric acid 10 g/l to 50 g/l or more); a sulfuric acid-phosphoric acid-aqueous hydrogen peroxide-water mixture (e.g., sulfuric acid 35 g/l, phosphoric acid 25 g/l, and aqueous hydrogen peroxide 10 g/l); a sulfuric acid-phosphoric acid-ascorbic acid-water mixture (e.g., sulfuric acid 35 g/l, phosphoric acid 25 g/l and ascorbic acid 10 g/l); a hydrochloric acid-aqueous hydrogen peroxide-formalin-water mixture (e.g., hydrochloric acid 40 mass %, aqueous hydrogen peroxide 2 mass % and formalin 10 mass %); or any other acidic electrolyte solution suitable for anodization of the metal of the medical device (14), the porous surface (14') of the medical device, or the optional metal coating material (16) applied to the porous surface of the medical device (100). Examples of alkaline electrolyte solutions (20) can include a potassium hydroxide-potassium fluoride-sodium phosphate-aluminum hydroxide-water mixture (e.g., potassium hydroxide 165 g/l, potassium fluoride 35 g/l, sodium phosphate 35 g/l and aluminum hydroxide 35 g/l) or any other alkaline electrolyte solution suitable for anodization of the metal of the medical device, the porous surface of the medical device, or the optional metal coating material applied to the porous surface of the medical device. It will also be understood by those of skill in the art that the solvent for the electrolytic solution (20) is not limited to water.

In some examples, the electrolyte solution (20) can comprise one or more organic solvents. In an example, the electrolyte solution (20) can also comprise a glycol, an emulsifier, a dispersant, a surfactant, or a combination thereof. In one example, the electrolyte solution (20) can further comprise about 1% to about 10%, by weight or by volume, of a glycol, an emulsifier, a dispersant, a surfactant, or a combination thereof. In another example, the electrolyte solution (20) can further comprise about 1% to about 10%, by weight or by volume, of ethylene glycol, propylene glycol, an emulsifier, a dispersant, a surfactant, or a combination thereof. In another example, the electrolyte solution (20) can comprise ethylene glycol or polyethylene glycol, or a combination thereof, at about 1% to about 10%, by weight or by volume, of the electrolyte solution (20). Without being bound by any particular theory, it is believed that the addition of a glycol, an emulsifier, a dispersant, a surfactant, or combination thereof, can improve the wetting property of the porous surface of the medical implant, including the wetting property of the optional metal coating material (16), by reducing the surface tension of the surfaces of the medical device, e.t., a porous surface (14), or by reducing the surface tension of the metal coating material (16) applied to the porous surface (14). The addition of a glycol, an emulsifier, a dispersant, a surfactant, or combination thereof, can also reduce the total electrical current created during the modified micro-arc oxidation processing according to one or more methods described herein.

In one example of modified micro-arc oxidation processing, the temperature of the electrolyte solution (20) can be about 10° C. or less. In another example, the electrolyte solution (20) can be at a temperature of about 5° C. or less. In still other examples, the electrolyte solution (20) can be at a temperature of about 2° C. or less. In some examples, the temperature of the electrolyte solution (20) is maintained at about 10° C. or less throughout application of an electrical signal and micro-arc oxidation processing. In other examples, the temperature of the electrolyte solution (20) can maintained at about 5° C. or less throughout application of an electrical signal throughout micro-arc oxidation processing. In yet another example, the temperature of the electrolyte solution (20) can maintained at about 2° C. or less throughout application of an electrical signal and micro-arc oxidation processing. Maintenance of a desired temperature of the electrolyte solution (20) at about 10° C. or less can be achieved by use of any known means, including pre-cooling the electrolyte solution (20) in a cooling device. In an example, the temperature of the electrolyte solution can be maintained throughout application of an electrical signal and the modified micro-arc oxidation processing by circulating the electrolytic solution (20) through a cooling device, e.g., circulating the electrolytic solution through a heat exchanger (30) configured to maintain the desired temperature of the electrolyte solution (20), e.g. at 10° C. or less, at 5° C. or less, or at 2° C. or less, as described above. In another example, the temperature of the electrolytic solution (20) can be maintained throughout application of a voltage and the modified micro-arc oxidation processing by continuously withdrawing the electrolyte solution (20) from the container (12), e.g., through a first pipe (32) and continuously adding through a second pipe (34) an electrolyte solution (20) that has been cooled to a desired temperature, e.g. cooled to a temperature of about 10° C. or less, to a temperature of 5° C. or less, and most preferably a temperature of about 2° C. or less. The electrolyte solution (20) can be cooled or the temperature of the electrolyte solution can be maintained during modified micro-arc oxidation processing by an electromechanical cooler (e.g. a thermoelectric heater/cooler or a heat exchanger), use of frozen blocks, use of frozen electrolyte solution, or any other knowns means for cooling a liquid.

In another example of a modified micro-arc oxidation process for modifying a porous surface of a medical device, the electrolyte solution (20) can be vigorously agitated throughout application of an electrical signal. In one example, vigorous agitation of the electrolyte solution (20) can include forming a vortex in the electrolyte solution (20). In another example, vigorous agitation can include causing the electrolyte solution (20) to form a vortex about the medical implant (100). In one example in which the electrolyte solution (20) is continuously introduced into the container (12), e.g., continuously recirculated through a heat exchanger (30), to maintain a selected temperature of the electrolyte solution (e.g., a temperature of about 10° C. or less, of about 5° C. or less, or of about 2° C. or less) during processing a porous surface of a medical device, the system (300, 400) can include a pipe coupling (38) configured to agitate the electrolyte solution (20) as it is introduced into the container (12), e.g., upon return to the container from a heat exchanger (30) through second pipe (34). In another example, an electrolyte solution (20) in the container (12)

can be withdrawn from the container (12) through first pipe (32), while fresh, cooled electrolyte (20) is added to the container (12) through a second pipe (34) to maintain a selected temperature of the electrolyte solution (20) in the container (12), and the second pipe (34) be fitted with a pipe coupling (38) configured to agitate the fresh, cooled electrolyte solution or to cause a vortex as the fresh, cooled electrolyte solution (20) is introduced into the container (12).

A cathode (18) for use in the modified micro-arc oxidation processing methods described herein can be submerged or immersed, partially or wholly, in an electrolyte solution (20). The cathode (18) can comprise any suitable metal material, e.g., a metal element or any combination of metal elements e.g., an alloy or a ceramic. In certain examples the cathode can comprise aluminum, stainless steel, titanium, vanadium, zirconium, hafnium, niobium, molybdenum, magnesium, tantalum, tungsten, chromium, cobalt, sodium, potassium, iron, calcium, copper, silver, gold, or any other known metal, metal alloy or ceramic. In certain examples, the cathode can comprise a sheet metal. The cathode (18) can have any size and can have any shape appropriate for the size and shape or surface area of the container (12), the medical device (100), or both. In one example, the cathode (18) for modified micro-arc oxidation processing of a porous medical device (100) can have a surface area greater than a surface area of the porous medical device (100). In another example, the cathode (18) can have a surface area that is three or more times greater than the surface area of the porous medical device (100). In one example, the cathode (18) can have dimensions of between about 12 inches and about 60 inches. In a preferred example, a cathode can be a sheet metal having dimensions of between about 24 inches to about 36 inches. It will be understood by those of skill in the art that if more than one implantable medical device (100) is to be processed at one time in the electrolyte solution (20) and the container (12), the surface area of the cathode (18) should be commensurate with the size of the processing container (12) and the surface area and the quantity of medical devices (100) to be processed at one time in the electrolyte solution (20) and the container (12).

An electrical power supply (500) can be used to supply an electrical signal to the medical device (100) and the cathode (18) when they are immersed or submerged in the electrolyte solution (20). The power supply (500) can be configured to supply direct current (DC), alternating current (AC), or a combination thereof, during the modified micro-arc oxidation processing described herein. In an example, the electrical signal can be in the form of a sine wave, a square wave, rectangular wave, triangular wave, a sawtooth wave, a pulsed wave, a rectified waveform of any of the foregoing waveforms, or any other known waveform; however, certain waveforms can result in consumption of large power, resulting in significant current and heat generation during application of the electrical signal. In preferred examples, as the modified micro-arc oxidation processing can be performed using a rectified waveform or a pulsed waveform, or a combination thereof. In one example the waveform can be a pulsed squared waveform as shown in FIG. 6. In still another example, the waveform can be a pulsed sine waveform as shown in FIG. 7. In yet another example, the waveform can be a rectified half sine wave, or a rectified full sine wave as shown in FIG. 8.

In one example, an electrical signal can have a peak voltage between about 50 V and 1000 V. In another example, an electrical signal can have a peak voltage between about 100 V and 800 V. In yet another example, an electrical signal can have a peak voltage between about 150 V and 500 V. In still another example, an electrical signal can have a peak voltage between about 200 V and 350 V. In one example the electrical signal can be applied to the medical device (100) and the cathode (18) for a period between 1 millisecond and 30 milliseconds. In another example, the electrical signal can be applied to the medical device (100) and the cathode (18) at a frequency (duty cycle) of between 10 Hz and 150 Hz. In an example, the electrical signal can be applied to the medical device (100) and the cathode (18) for 1 millisecond and a frequency of 10 Hz.

As shown in FIGS. 9A and 9B, the modified micro-arc oxidation process described herein results in the anodization current decreasing relative to voltage, which indicates the formation micro-pores in a porous oxide layer (14') on the porous surface (14) of the medical device (100), as can be seen in FIGS. 5A and 5B. The modified micro-arc oxidation process described above can reduced the total current in the system. As seen in FIG. 9A, the standard micro-arc oxidation process curve exhibits large current between 10 V to 20 V and again above 100 V. In this example, the standard micro-arc oxidation process had to be abandoned at 100 V because of the increasing current. As seen in FIG. 9A, the modified micro-arc oxidation process curve exhibits a much smaller current and the process continued to completion at 120V. This end of the modified micro-arc oxidation process is shown separately in FIG. 9B. A seen in FIGS. 9A and 9B, the current in the standard micro-arc oxidation process continues to increase, whereas the modified micro-arc oxidation process continues to completion with the current decreasing during processing above 100 V.

In a preferred example, a modified micro-arc oxidation processing method can include depositing a metal coating material (16) on a porous surface (14) of a medical device (100), immersing at least a portion of the porous surface (14) in an acidic or alkaline electrolyte solution (20), maintaining an electrolyte solution (20) at a temperature of about 10° C. or less, at a temperature of about 5° C. most preferably at about 2° C. or less, and applying an alternating current as a rectified sine wave with RMS voltage of 200V and peak voltage of 272V. In still another example of a modified micro-arc oxidation process for modifying a porous surface of a medical device, ultrasonic waves (U) can be introduced into to the electrolyte solution (20) prior to and/or during application of the electrical signal. In one example, ultrasonic waves (U) can be introduced into the electrolyte solution using an immersible ultrasonic transducer (50) as described above. In another example, the container (12) can be immersed in a cooling tank (26), e.g., including a coolant (28), and ultrasonic waves (U) can be introduced into the coolant (28) using an immersible ultrasonic transducer (50). The ultrasonic waves (U) facilitate electrolyte flow and penetration of crevices and macro-pores of the porous surface (14), thereby reducing crevice corrosion. Without being bound by any particular theory, it is believed that the improved electrolyte flow through macro-pores and crevices also facilitates heat transfer, increases the supply of oxygen to the macro-pores and crevices, and prevents reduction of localized pH in the macro-pores and crevices of the porous surface (14) of the medical device (100). Introduction of ultrasonic waves (U) to the electrolyte solution (20) or to the cooling solution (28) dramatically decreases the total current consumed in the process and switching off the ultrasonic waves (0 during modified micro-arc oxidation processing results in a sudden jump in current.

It will be understood by those skilled in the art that a peak voltage, a signal duration, and a signal frequency (duty cycle) of an electrical signal can each be selected to obtain a desired feature in the modified porous surface (14) of the medical device. In an example, a peak voltage of 50 V to 150 V can be sufficient to create a thicker oxide layer of between about 1 nanometer and about 5 microns. In preferred example a peak voltage of about 150 V to about 1000 V is sufficient to cause electrical discharge or sparking at the porous surface (14) of the medical device (100), creating micro-pores (FIGS. 5A, 5B) in the surfaces that form the macro-pores defining the porous surface (14) of the medical device (100). The modified porous surface (14') comprising micro-pores formed by the modified micro-arc oxidation processing can have a diameter of about <1 μm (submicron diameters) to about 5 μm. As will be understood by those skilled in the art, the size, shape, depth and overall morphology of the micro-pores of the modified porous surface (14') of the medical device (100), produced by the modified micro-arc oxidation processing, can be varied based upon the selected peak voltage, the selected frequency (duty cycle) of application of the electrical signal, the selected time of application of the electrical signal, the selected composition of the electrolyte solution (20), the selected temperature of the electrolyte solution (20), and, optionally, the application of a coating material (16), or the application of ultrasonic waves (U), or the inclusion of an additive (a glycol, emulsifier, a dispersant, a surfactant, or a combination thereof) in the electrolyte solution (20).

In another example, areas of a medical device where micro-arc oxidation are not desired, e.g., a taper connection, a locking groove, articulating surfaces, a smooth surface (10), or other select areas of a porous surface (14) can be masked with a masking material (42) to seal or protect the area from the electrolyte solution (20) and the current or voltage generated during the modified micro-arc oxidation process described herein, and to deter anodization of the masked portion of the medical device (100). In one example, a masking material (42) can comprise a composition that can be applied to a selected surface of the medical device (100) where micro-arc oxidation processing is not desired. In another example, as shown in FIG. 13B, the masking material (42) can comprise a device, e.g. a cover and/or a seal, that can be applied over a select surface of the medical device (100) where micro-arc oxidation processing is not desired. In FIG. 13B, an acetabular cup prosthesis in the form of a semi-hemisphere comprises an outer porous surface (14) and an inner smooth surface (10), and a masking material (42) comprising a cap and a seal are provided to protect the inner smooth surface (10) during anodization of the porous surface (14). In one example, the masking material can be applied to one or more areas of a porous medical device (100) to provide a substantially liquid tight seal around the area to which the masking material is applied. In another example, a masking material (42) can be configured to withstand an acidic electrolyte solution (20). In another example, a masking material (42) can be configured to withstand an alkaline electrolyte solution (20). In another example, a masking material (42) can be configured to withstand a high voltage, a high current, or both, e.g., a voltage of between about 100 V to about 1000 V. In another example a masking material (42) can be configured to withstand a high temperature, e.g., a temperature resulting from sparking during micro-arc oxidation. In one example, the masking material (42) can be configured to withstand a temperature of about 3,000 K. In one example, a masking composition (42) can comprise silicone rubber with silicone dioxide filler, e.g., silica or fumed silica, with titanium dioxide filler, iron oxide filler, or a combination thereof. In another example, a masking material (42) can comprise a silicone rubber with one or more filler materials configured to impart dielectric, heat transfer and/or mechanical strength to the masking composition. In an example, the filler of a masking material (42) can comprise alumina trihydrate, zinc oxide, titanium dioxide, calcium carbonate, barium titanate, carbon-black particles, or a combination thereof.

As shown in FIGS. 4 and 10, there is provided a system and method to process several porous medical devices (14) simultaneously using any one or any combination of the modified micro-arc oxidation processes described herein, in a single container (12) of electrolyte solution (20). In a system and method of processing multiple porous medical devices (100) simultaneously in a single container (12) of electrolyte solution, the current requirements and cathode (18) surface area requirements for a single medical device can be multiplied by the number of porous medical devices (100) being processed in a single container of electrolyte solution. In one example, a plurality of medical devices (100) can comprise at least a first medical device (100(1)) and a second medical device (100(2)). In one example the system can comprise a container (12) for holding an electrolyte solution (20), a cathode (18) connected to an electrical power supply (500), and a plurality of electrodes or wires (22) for electrically connecting a plurality of medical devices (100(1), 100(2), etc.) and a cathode (18) to the power supply (500). In an example, the plurality of medical devices (100(1), 100(2), etc.) can be electrically connected to an electrical power supply (500) through a wire (22). In one example, a plurality of medical devices (100(1), 100(2), etc.) can be electrically connected to a bus (24) through a wire (22) and the bus (24) can be electrically connected to a power supply through a wire (22). In a preferred example, each one of the plurality of medical devices (100(1), 100(2), etc.) can be electrically connected by a wire (22) to an electrical power supply (500).

In some examples the system comprises a heat exchanger (30) and a system of pipes or tubing (32, 34) to circulate an electrolyte solution (20) or a cooling solution (28) through the heat exchanger (30). In another example, the system can comprise a pump (36) configured to facilitate circulation of an electrolyte solution or a cooling solution through a heat exchanger (30). In one example, the system can also comprise a controller (510) electrically connected to an electrical power supply (500) and the plurality of medical devices (100a, 100b, etc.) to control sequencing of the application of an electrical signal (sometimes referred to herein as a voltage) to each one of the plurality of medical devices (100a, 100b, etc.). In one example, the plurality of medical devices (100(1), 100(2), etc.) can be electrically connected by a wire (22) to a controller (510) and the controller can be electrically connected to an electrical power supply (500). In an example, a controller (510) can comprise a switch electrically connected to an electrical power supply (500) and to at least one of the plurality of medical devices (100(1), 100(2), etc.). In another example, a controller can comprise a plurality of switches electrically connected to a plurality of wires (22) that can be electrically connected to a plurality of medical devices (100(1), 100(2), etc.). In a preferred example, a plurality of switches can correspond to a plurality of medical devices such that one switch is electrically connected to one of the plurality of medical devices. In yet another example, a controller (510) can comprise a circuit board electrically connected to the plurality of medical devices (100(1). 100(1), etc.) and to the electrical power supply (500). In a preferred example, a controller (510) can comprise a low voltage circuit board. In another example, the system can comprise a plurality of relays (520) electrically connected to a controller (510) and to each one of the plurality of medical devices (100(1), 100(2), etc.). In a preferred example, a relay (520) can be a high voltage relay. In a preferred example, the system comprises a low voltage circuit board (510) and a high voltage relay (520) electrically connected to each other and to an electrical power supply. In one example, the controller is configured to automatically sequence the application of an electrical signal and/or the timing of the application of an electrical signal to the plurality of medical devices (100(1), 100(2), etc.). In a preferred example, a circuit board is configured to automatically control the application of an electrical signal and/or the timing of application of an electrical signal to the plurality of medical devices (100(1), 100(2), etc.).

In another example, a system for processing a plurality of medical devices (100(1), 100(2), etc.) in a container (12) of electrolyte solution (20) can comprise a means for data acquisition (600, 610, 620, 630). In one example, the means for data acquisition can comprise one or more sensors or probes (610, 620, 630) for detecting a parameter of modified micro-arc oxidation processing according to any of the examples disclosed herein. In an example, a sensor or probe can detect a current or amperage (610). In a preferred example, a plurality of probes to detect a current or amperage (610) can be electrically connected to corresponding plurality of medical device (100(1), 100(2), etc.), such that one probe is electrically connected to one medical device, and to a controller (510) and/or a relay (520). In a preferred example, plurality of probes (610(1), 610(2), etc.) to detect a current or amperage can be electrically connected to the plurality of medical devices (100(1), 100(2), etc.) and to a corresponding plurality of relays (520(1), 520(2), etc.). In a preferred example, a plurality of probes to detect a current or amperage (610(1), 610(2), etc.) can be electrically connected to corresponding plurality of medical devices (100(1), 100(2), etc.), such that one probe is electrically connected to one medical device, and can be electrically connected to a plurality of relays (520(1), 520(2), etc.), such that one probe is connected to one relay, and each one of the plurality of relays (520(1), 520(2), etc.) can be electrically connected to a controller (510).

In another example, the sensor or probe of the system can detect a voltage (630). In another example, the sensor or probe can detect a temperature of an electrolyte solution (620). Data from a sensor or probe (610, 620, 630) can be supplied to a data acquisition device (600), e.g., a monitor, a printer, or a computer or other device configured to record data from a sensor or a probe (610, 620, 630), such that the data can be recorded and/or viewed by a user. One of ordinary skill in the art will understand the system described herein for processing a plurality of medical devices using modified micro-arc oxidation processing, can also be used to simultaneously process a plurality of medical devices using a standard micro-arc oxidation process to process a plurality of medical devised in a single container of electrolyte solution.

The system described herein, for example as shown in FIG. 10, for simultaneously processing a plurality of medical devices in a single container of electrolyte solution, can be used in a modified micro-arc oxidation process according to any of the methods described herein. In an example of modified micro-arc oxidation processing of multiple porous medical devices (100) simultaneously in a single container (12) of electrolyte solution (20), the electrical signal can be sequenced such that only a single porous medical device (100) can receive an electrical signal from an electrical source (500) at any given time. Thus, the cathode (18) area requirement for a single porous medical device can be used in this modified micro-arc oxidation sequencing process to sequentially deliver a desired voltage to a select one of a plurality of medical devices (100(1), 100(2), etc.). In one example, this modified micro-arc oxidation sequencing process is performed automatically by a controller (510) to sequentially deliver a desired voltage to each one of the plurality of medical devices (100(1), 100(2), etc.) in an electrolyte solution (20). The timing and distribution of current, to each medical device (100 (100(1), 100(2), etc.) can be controlled by a controller (510), e.g., a manual controller or an automated controller (510).

In one example, a controller (510) can be used to control a sequencing of an electrical signal supplied by the electrical power supply. In an example, a controller (510) can be used to control application of a voltage to the plurality of medical devices (100(1), 100(2), etc.). In another example, a controller can be used to control timing of an application of a voltage to the plurality of medical devices (100(1), 100(2), etc.). In a preferred example of the method, a circuit board (510) can be used to control an electrical signal received from a power supply (500). In a preferred example, a circuit board (510) can sequentially supply an electrical signal to a select one of the plurality of relays (520(1), 520(2), etc.) (i.e., one relay at a time receives the electrical signal) to open or close the select one of the plurality of relays. In one example, a circuit board can sequentially supply an electrical signal to a select one of the plurality of relays (520(1), 520(2), etc.) to open the select one of the plurality of relays to complete the electrical circuit from the electrical power supply (500), through a select one of the plurality of medical devices (100(1), 100(2), etc.) connected to the select relay, through the electrolyte solution (20), through the cathode (18), and back to the power supply (500).

In a preferred example, a circuit board (510) can sequentially supply an electrical signal to a select one of the plurality of relays (520(1), 520(1), etc.) to close the select relay to complete the electrical circuit from the electrical power supply (500), through the select relay (520(1), 520(1), etc.), the select medical device (100(1), 100(2), etc.) connected to the select relay, through the electrolyte solution (20), through the cathode (18), and back to the power supply (500). In another example, amperage probes (610(1), 610(2), etc.) on each anode wire (22) are connected to a data acquisition system (600) to acquire data regarding current during application of an electrical signal. In another example, a temperature probe, e.g., a thermocouple (620) can be used to acquire a record of a temperature of the electrolyte solution (20) or a cooling solution (28) during processing. In yet another example, a voltage probe (630) can be used to acquire voltage data during processing.

In one example a high voltage relay (520) can be electrically connected to the controller and to each one of the probes (610). In another example, a plurality of probes (610) coupling the controller (510) to each one of the medical devices (100), can be used to acquire data for delivery to a data acquisition system (600), e.g. a computer, to record data related to the processing of each one of the plurality of medical devices (100). In another example, a temperature sensors or probe (610) and/or a voltage probe (630) for detecting parameters of the processing system, can be electrically connected to a data acquisition system (600). FIG. 11 illustrates data acquired from amperage probes (610(1), 610(2)), anode/medical device (100(1), 100(2), etc.), cathode (18), and a thermocouple (620) in the electrolyte solution during sequential anodization of six medical devices (100(1), 100(2), etc.). In one example, the sequencing process described above can be performed at any peak voltage, frequency (duty cycle), or other electrical parameters described above for any example of a modified micro-arc oxidation process.

By controlling the waveform used in a modified micro-arc oxidation process, as described above, and sequentially applying a voltage and waveform to each individual medical device (100(1), 100(2), etc.) to be simultaneously processed in a single electrolyte solution (20), a preferred voltage, a preferred waveform and preferred pulse frequency can be separately provided to each one of the plurality of medical devices (100(1), 100(2), etc.). Sequencing of voltage application to a plurality of medical devices (100(1), 100(2), etc.) in one electrolyte solution (20) can also be applied to non-porous medical devices and to non-porous e.g., smooth surfaces (10) of porous medical devices (100) to reduce the current, cathode surface area requirement, and electrolyte requirement for processing multiple medical devices (100*a*, 100*b*, etc.) in a single container (12) of electrolyte solution (20). The system and sequencing process for processing a plurality of medical devices in a single electrolyte solution using a micro-arc oxidation process, can also be used for processing a medical device having a smooth surface (10) and a porous surface (14) or a modified porous surface comprising micro-pores (14'), to deposit a bioactive agent or a therapeutic agent, simultaneously, on different surfaces of the medical device as described below. The system and sequencing process for processing a plurality of medical devices in a single electrolyte solution using a micro-arc oxidation process, can also be used for processing a plurality of medical devices (100(1), 100(2), etc.) having a smooth surface (10) and a porous surface (14) or a modified porous surface comprising micro-pores (14'), to deposit a bioactive agent or a therapeutic agent, simultaneously, on different surfaces of each one of the plurality of medical devices as described below.

The modified porous surface (14') of the implantable medical device (100), processed according any one of the methods of modified micro-arc oxidation described herein, includes micro-pores (FIGS. 5A, 5B) that can readily adsorb a therapeutic or bioactive agent (collectively referred to herein as a "therapeutic agent). A therapeutic agent can be applied to the modified porous surface of the medical device by any conventional means, e.g., immersion, brushing, spraying, electrophoresis, or a combination thereof, to form a medical device (100) having a smooth surface with a therapeutic agent (10') and a porous surface (e.g., a modified porous surface) with a therapeutic agent deposited thereon (14'). Therapeutic agents that can be adsorbed by on a smooth surface (10) of a medical device, on a porous surface (14) of a medical devices, and on a modified porous surface, comprising micro-pores (14') of a medical device (including, without limitation, a modified porous surface comprising micro-pores and prepared by the modified micro-arc oxidation methods disclosed herein), include, without limitation, osteoinductive compounds (e.g., bone morphogenetic proteins and other growth factors, and stromal cell-derived factor 1α and other chemokines), osteoconductive compounds (e.g., hydroxyapatite or other calcium phosphate compounds), chitosan, collagen or collagen mimetic peptides, hyaluronic acid, lauric acid, polymer brush coatings (e.g., arginine-lysine-aspartic acid ligand (RGI) ligand), polyethylene glycol, poly(methyl methacrylic acid) (PMMA), antibiotics, antimicrobial peptides, zinc compounds, copper compounds, bismuth compounds, gold, palladium, silver and compounds thereof, iodine compounds (e.g., inorganic compounds such as silver iodide, potassium iodide, nickel iodide, iron iodide and tin iodide; organic compounds, for example, chain saturated hydrocarbons and their derivatives such as methyl iodide, ethyl iodide, propyl iodide, butyl iodide, and isopropyl iodide; chain unsaturated hydrocarbons and their derivatives such as vinyl iodide, anyl iodide, crotyl iodide, propargyl iodide, and phenylacetylene iodide; aromatic hydrocarbons and their derivatives such as iodobenzene, benzyl iodide, benzoyl iodide, phenacyl iodide, xylylene iodide, phthalein iodide, hydroquinone iodide, and cyclodextrin-iodine inclusion compounds; hetero-compounds such as trimethylsulfonium iodide and triphenyl-sulfonium iodide; and hetero-compound polymers such as polyvinyl pyrrolidone iodine and polyvinyl-phthalimide iodine).

A medical device (100) can have areas of porous surfaces (14), areas of modified porous surfaces comprising micropores (14'), and areas of smooth or non-porous surfaces (10). The surface area differences between porous surfaces (14), modified porous surface (14'), and non-porous (smooth) surfaces (10) draws different current during electrodeposition of a therapeutic agent, resulting in varied concentration of a therapeutic agent adsorbed on the porous surfaces (14), the modified porous surfaces (14'), and on the non-porous surfaces (smooth surfaces) (10) of the same medical device (100). The amount or concentration of a therapeutic agent adsorbed on a surface of a medical device (100), e.g., a smooth surface (10), or a porous surface (14), or a modified porous surface comprising micro-pores (14'), can be controlled using an electrodeposition system (including a modified micro-arc oxidation system, such as those described above or as shown in FIGS. 2, 3 and 4) and using a method comprising (i) controlling a cathode in the electrical circuit, (ii) controlling an electrolyte solution (20) exposed to a surface(s) of the medical device (100) intended to receive a deposit of a therapeutic agent, and/or (iii) controlling a temperature of an electrolyte solution (20) exposed to a surface of the medical device (100) intended to receive a deposit of a therapeutic agent.

In one example, a system (200, 300, 400,700, 800) for depositing a therapeutic agent on a surface of a medical device comprises an electrolytic cell comprising a container (12), a cathode (18), a medical device (100) as an anode, and an electrolyte solution mixed with a therapeutic agent (20). In an example, the container (12) can be configured to hold a volume of an electrolyte solution and a volume of a therapeutic agent (20), the total volume of electrolyte solution and therapeutic agent (20) being sufficient to cover a surface (10, 14, 14') of the medical device (100) intended to receive a deposit of a therapeutic agent. In certain examples, the system (200, 300, 400, 700, 800) can include a removable ultrasound transducer (50) configured to be immersed in a solution (20) of the electrolyte and therapeutic agent. The medical device (100), which serves as the anode, and the cathode (18) are each configured to be connected by a wire (22) to an electrical power source (500). In one example, the medical device (100), the cathode (18), or both, can be mounted on or electrically coupled to a holder or bus bar (24). In another example, the medical device (100), the cathode (18), or both, can mounted on or electrically connected by a wire (22) to a bus bar (24) and the bus bar (24) can be electrically connected by a wire (22) to an electrical power source (500).

Electrolyte solutions (20) that can be used in the processes described herein for depositing a therapeutic agent on a surface of a medical device can include any electrolytic solution suitable for the therapeutic agent being deposited on the surface of the medical device. In one example, the electrolyte solution can be a salt solution. In a preferred example, the electrolyte solution can comprise a silver salt solution. In another preferred example, the electrolyte solution can comprise an iodine salt solution. In another preferred example, the electrolyte solution can comprise iodine poly(vinylpyrolidone). In another example, the electrolyte solution can be an acidic or alkaline electrolyte solution or any combination of electrolyte solutions suitable for a therapeutic agent and suitable for a metal of the medical device. In certain examples the electrolyte solution can be an acidic electrolytic solution, which can include a combination of electrolytes to form an acidic electrolyte solution. In other examples the electrolyte solution can be an alkali electrolytic solution, which can include a combination of electrolytes to form an alkaline electrolyte solution. One of ordinary skill in the art will understand that the electrolyte solution (20) selected should be one that is appropriate for the therapeutic agent and the metal composition of the surface of the medical device, e.g., a smooth surface (10), or a porous surface (14), or a modified porous surface comprising micro-pores (14'). Examples of acidic electrolyte solutions and alkali electrolyte solutions (20) that can be used in the therapeutic agent deposition methods described herein can include those disclosed herein for use in a modified micro-arc oxidation method, or any other acidic electrolyte solution or alkaline electrolyte solution, that is suitable for the therapeutic agent and suitable for the metal of the medical device (100), a metal of a smooth surface of the medical device, a metal of a porous surface (14) of the medical device, or a metal of a modified porous surface comprising micro-pores (14') of the medical device, intended to receive a deposit of a therapeutic agent.

In one or more examples described below, electrodeposition of a therapeutic agent on a first surface (10, 14, 14') and a second surface (10, 14, 14'), different from the first surface, can occur simultaneously in a single electrolytic cell or in separated electrolytic cells, such as in separate containers (12, 12A, 12B), or in separate compartments (13A, 13B) of a single container (12). In such separated electrolytic systems, and methods using such systems, a first electrolyte solution/therapeutic agent (20) can be disposed in a first container or compartment (12A, 13A), and a second electrolyte solution/therapeutic agent (20) can be disposed in a second container or compartment (12B, 13B). As one of skill in the art will understand, by providing separate electrolytic cells for processing different surfaces (10, 14, 14') of a medical device, the electrolyte solution and/or its concentration can vary between the first container or first compartment (12A, 13B) and the second container or second compartment (12B, 13B). Similarly, by providing separate electrolytic cells for processing different surfaces (10, 14, 14') of a medical device, the therapeutic agent and/or its concentration can vary between the first container or first compartment (12A, 13A) and the second container or second compartment (12B, 13B), in one example the first electrolyte solution/therapeutic agent (20) and the second electrolyte solution/therapeutic agent (20) can comprise the same electrolyte solutions at the same concentrations, and the same therapeutic agents at the same concentrations. In some preferred examples, the first electrolyte solution/therapeutic agent (20) and the second electrolyte solution/therapeutic agent (20) can comprise the same electrolyte solution at different concentrations. In other preferred examples, the first electrolyte solution/therapeutic agent (20) and the second electrolyte solution/therapeutic agent (20) can comprise different electrolyte solutions at the same concentrations and/or different concentrations. In still other examples, the first electrolyte solution/therapeutic agent (20) and the second electrolyte solution/therapeutic agent (20) can comprise the same therapeutic agent at different concentrations. In a preferred example, the concentration of a therapeutic agent in an electrolyte solution suitable for processing a smooth surface (10) of a medical device can be less than a concentration of the same therapeutic agent in an electrolyte suitable for processing a porous surface or modified porous surface comprising micro-pores (14') on the same medical device. In a preferred example, the therapeutic agent can be at a concentration in the electrolyte solution (20) sufficient to deposit from about 0.1 $\mu g/cm^2$ to about 1,000 $\mu g/cm^2$ or more of the therapeutic agent on a surface (10, 14, 14') of the medical device (100). In one example, the therapeutic agent comprises iodine and can be at a concentration in the electrolyte solution sufficient to deposit at least between about 0.1 $\mu g/cm^2$ and about 500 $\mu g/cm^2$ on a surface (10, 14, 14') of a medical device. In a preferred example, the therapeutic agent is iodine and can be at a concentration in the electrolyte solution sufficient to deposit between about 20 $\mu g/cm^2$ and about 100 $\mu g/cm^2$ on a porous surface (14) or a modified porous surface (14') comprising micro-pores. In another example, the therapeutic agent in silver and can be at a concentration in the electrolyte solution sufficient to deposit between about 0.2 $\mu g/cm^2$ and about 200 $\mu g/cm^2$. In a preferred example, the therapeutic agent is silver and can be at a concentration in the electrolyte solution sufficient to deposit between about 2 $\mu g/cm^2$ and about 20 $\mu g/cm^2$ on a porous surface (14) or on a modified porous surface (14') comprising micro-pores. Concentrations for other therapeutic agents can be at concentrations in the electrolyte solution sufficient to deposit on a surface of the medical device any desired concentration of the therapeutic agent (e.g., $\mu g/cm^2$, $mg/cm^2$, or $g/cm^2$) that is known to be effective for treatment using the therapeutic agent.

It will also be understood by those of skill in the art that the solvent for the electrolytic solution and/or a therapeutic agent (20) is not limited to water. In some examples, the electrolyte solution, the therapeutic agent, or a mixture thereof (20) can comprise one or more organic solvents. In an example, the electrolyte solution/therapeutic agent (20) can also comprise a glycol, an emulsifier, a dispersant, a surfactant, or a combination thereof. In one example, the electrolyte solution/therapeutic agent (20) can further comprise about 1% to about 10%, by weight or by volume, of a glycol, an emulsifier, a dispersant, a surfactant, or a combination thereof. In another example, the electrolyte solution/therapeutic agent (20) can further comprise about 1% to about 10%, by weight or by volume, of ethylene glycol, propylene glycol, an emulsifier, a dispersant, a surfactant, or a combination thereof. In another example, the electrolyte solution/therapeutic agent (20) can comprise ethylene glycol or polyethylene glycol, or a combination thereof, at about 1% to about 10%, by weight or by volume, of the electrolyte solution/therapeutic agent (20).

The systems (200, 300, 400, 700, 800) for depositing a therapeutic agent on a surface of a medical device can be configured with a means to heat, cool or maintain a desired temperature of the electrolyte solution/therapeutic agent (20) during processing. In one example, the system (200) can include a cooling tank (26) configured to hold a cooling solution (28), e.g., water, antifreeze, or other coolant. The cooling tank (26) can be configured to hold the container (12) at least partially immersed in a cooling solution (28) during therapeutic agent deposition processing of the medical device (100). In another example, the system (300, 400, 700, 800) can comprise one or more devices to heat or chill a fluid, e.g., a thermoelectric heater, a thermoelectric chiller, or a thermoelectric heater/chiller (such devices are sometimes collectively referred to herein as "heat exchangers") (30) to cool or maintain a desired temperature of the electrolyte/therapeutic agent solution (20), the cooling solution (28), or both. To maintain a desired temperature of a cooling solution (28), an electrolyte solution/therapeutic agent (20), or both, e.g., at about 10° C. or below 10° C., during processing, the solution (20, 28) can be withdrawn from the container (12) through a first pipe (32), circulated through a heat exchanger (30), and can be passed from the heat exchanger (30) through a second pipe (34) and reintroduced into the container (12). The operation of the heat exchanger (30) can be controlled automatically to maintain the desired temperature of the electrolyte solution/therapeutic agent (20). In one example, the system (300, 400, 700, 800) can comprise a pump (36) configured to withdraw the solution (20, 28) from the container (12, 26) and into the heat exchanger (30). In a preferred example, the heat exchanger (30) can be a plate heat exchanger. In another example, the first pipe (32) can be disposed in a lower portion of the container (12). In another example the first pipe (32) can be a connected to a bore (40) formed in a lower portion of the container (12), e.g., a lower wall or bottom wall (19) of the container (12). As one of skill in the art will understand, by providing separate electrolytic cells for processing different surfaces (10, 14, 14') of a medical device, the temperature of the electrolyte solution/therapeutic agent (20) can vary between the first container or first compartment (12A, 13B) and the second container or second compartment (12B, 13B). Similarly, by providing separate electrolytic cells for processing different surfaces (10, 14, 14') of a medical device, the temperature of an electrolyte solution/therapeutic agent (20) can be maintained at different temperatures between the first container or first compartment (12A, 13A) and the second container or second compartment (12B, 13B). Also, by providing separate electrolytic cells for processing different surfaces (10, 14, 14') of a medical device, the temperature of an electrolyte solution/therapeutic agent (20) can be maintained at different temperatures between for processing a smooth surface (10) and for processing a porous surface (14) or a modified porous surface comprising micro-pores (14').

In still another example the therapeutic agent deposition system (200, 300, 400, 700, 800) can be configured with an agitator (38) to create vigorous agitation in the electrolyte solution/therapeutic agent (20). In one example, the agitator can comprise a means to mechanically stir the electrolyte solution/therapeutic agent, e.g., a magnetic stirrer. In another example, the agitator (38) can comprise a feature disposed adjacent to a second pipe (34), configured to cause turbulence or to create a vortex about the medical device (100) as the electrolyte solution/therapeutic agent (20) is passed through the second pipe (34) and into the container (12). In a preferred example, an agitator (38) can comprise a pipe coupling that creates vortex in the electrolyte solution/therapeutic agent (20). In certain examples, the pipe coupling (38) can comprise an angled pipe configured to circulate the electrolyte solution/therapeutic agent (20) entering from the second pipe (34) about the medical device (100). In another example, the system (200, 300, 400, 700, 800) can comprise an agitator (38) in the form of both a mechanical stirrer and a pipe coupling coupled to the second pipe (34).

In other examples, as shown in FIGS. 12A, 12B and 12C, systems and methods are provided to deposit a therapeutic agent simultaneously on one or more surfaces of a medical device, e.g., a smooth surface (10), a porous surface (14), a modified porous surface comprising micro-pores (14'). In an example, the system comprises an electrolytic cell comprising a container (12), an electrolyte solution and a therapeutic agent (20), a cathode (18), and an anode comprising the medical device (100). In an example, the container can be configured to hold a medical device. In one example, as show in FIGS. 12A and 12B, the container can comprise a first container (12A) and a second container (12B). In a preferred example, the first container (12A) can include an aperture (15) configured to permit a portion of a medical device to extend therethrough such that a first surface (10, 14, 14') of a medical device (100) can be processed in the first container (12A) while a second surface (10, 14, 14') of the medical device, different from the first surface, is simultaneously processed in the second container (12B). In one example, a system can comprise a masking material (42), e.g., a seal, at an aperture (15) of the first container to provide a barrier between a first container (12A) and a second container (12B), and to separate the electrolytic reactions occurring in the first container and the second container. In another example (FIG. 12A), one of the first container (12A) and the second container (12B) can be configured to seat in the other one of the first container (12A) and the second container (12B).

In another example (FIG. 12B), a container (12) can comprise a first compartment (13A) and a second compartment (13B), each of the first compartment and second compartment configured to hold an electrolyte solution/therapeutic agent (20). In one example, the first compartment (13A) and second compartment (13B) can be formed by a divider (17) extending between walls (19) of the container (12). In one example, the system can comprise an aperture (15) between the first compartment (13A) and the second compartment (13B), such that a first surface (10, 14, 14') of a medical device (100) can be seated in the first compartment (13A), and a second surface (10, 14, 14') of the medical device (100), different from the first surface, can be seated in the second compartment (13B). In a preferred example, the system can comprise a masking material (42), e.g., a seal disposed about the aperture (15) to provide a barrier between the first compartment (13a) and the second compartment (13B), and to separate electrolytic reactions occurring in the first compartment and the second compartment. In a preferred example, an aperture can be disposed in a divider (17), and a seal (42) can surround the aperture. In one example, the seal can comprise a polypropylene seal. One of skill in the art will understand that any select surface (10, 14, 14') of a medical device (100) can be seated in either a first container/first compartment, or a second container/second compartment, provided that a selected second surface (10, 14, 14') of the medical device, different from the first surface, is seated in the other one of the first container/first compartment, or a second container/second compartment.

In another example, as shown in FIGS. 12C, 13A and 13B, a medical device (100) can comprise an exterior porous surface (14) or an exterior modified porous surface comprising micro-pores (14'), and an interior smooth surface (10). In one example, an interior smooth surface (10) can form a cavity. In a preferred example, an interior smooth surface (10) of a medical device can define a cavity configured to hold a volume of an electrolyte solution/therapeutic agent (20). In a preferred example, the medical device (100) can comprise a cup-shape having an exterior porous surface (14) or an exterior modified porous surface comprising micro-pores (14'), and an interior smooth surface (10). In another preferred example, the medical device (100) comprises an acetabular cup having an interior smooth surface (10) that can define a cavity configured to hold a volume of an electrolyte solution/therapeutic agent (20). In another example, a medical device comprising an interior smooth surface (10) can be configured to isolate the interior surface from an environment of the exterior porous surface (14) or the exterior modified porous surface (14'), e.g., an electrolyte solution electrolyte solution/therapeutic agent in a container (12) in which processing of the exterior surface occurs. In one example, the system can comprise a masking material (42) configured to provide a barrier to the interior porous surface (10) of the medical device (100). In another example, the masking material (42) can comprise a cap or cover, a seal, or both, to provide a harrier between the interior smooth surface (10) and the exterior porous surface (14) or exterior modified porous surface (14') of the medical device (100). In another example, the system can comprise a first cathode (18A) electrically connected to an exterior porous surface (14) or to an exterior modified porous surface (14') of a medical device, and a second cathode (18B) electrically connected to an interior smooth surface of the medical device.

In an example, a cathode (18) of a system (200, 300, 400, 700, 800) for electrodeposition of a therapeutic agent on a surface of a medical device can comprise one or more walls (19) of the container (12, 12A, 12B). In another example, a cathode (18) can comprise a piece of metal separate from the container (12). In one example, the cathode can be of a size, a shape, or both, to substantially mimic or conform to a size, a shape, or both, of the container (12). A cathode (18) can comprise any suitable metal material, e.g., a metal element or any combination of metal elements e.g., an alloy or a ceramic. In certain examples, a cathode can comprise aluminum, stainless steel, titanium, vanadium, zirconium, hafnium, niobium, molybdenum, magnesium, tantalum, tungsten, chromium, cobalt, sodium, potassium, iron, calcium, copper, silver, gold, or any other known metal, metal alloy or ceramic. In certain examples, the cathode can comprise a sheet metal.

In an example a system (200, 300, 400, 700, 800) for electrodeposition of a therapeutic agent on one or more surfaces of a medical device (100), can comprise a cathode (18) having any size and/or any shape appropriate for the size and shape of the container or a compartment therein (12, 12A, 12B, 13A, 13B) or of the medical device (100), or appropriate for the surface area of the container/compartment (12, 12A, 12B, 13A, 13B), or the surface area of the medical device (100), or the surface area for a select surface of the medical device intended to receive a deposit of a therapeutic agent, e.g., a select smooth surface (10), a select porous surface (14), or a select modified porous surface comprising micro-pores (14'). In one example, a cathode (18) can have a surface area greater than a surface area of the medical device (100), or greater than a surface area of a select surface of the medical device intended to receive a deposit of a therapeutic agent, e.g., a select smooth surface (10), a select porous surface (14), or a select modified porous surface comprising micro-pores (14'). In another example, a cathode (18) can have a surface area that is three or more times greater than the surface area of the medical device (100) or the surface area of a select surface of the medical device intended to receive a deposit of a therapeutic agent, e.g., a select smooth surface (10), a select porous surface (14), or a select modified porous surface comprising micro-pores (14'). It will be understood by those of skill in the art that if more than one implantable medical device (100) is to be processed at one time in the electrolyte solution/therapeutic agent (20) of the container or compartment (12, 12A, 12B, 13A, 13B), the surface area of the cathode (18) should be commensurate with the size of the processing container or compartment (12, 12A, 12B, 13A, 13B) and the surface area and the quantity of medical devices (100) to be processed at one time in the electrolyte solution/therapeutic agent (20). In one example, a cathode (18) can comprise a plurality of cathodes (18), such as at least a first cathode (18A) and a second cathode (18B).

In some examples (e.g., FIGS. 12B and 12C), the system can comprise a heat exchanger (30), in fluid communication with a container (12, 12A, 12B) or compartment within a container (13A, 13B), to heat or chill an electrolyte solution and therapeutic agent (20), or to maintain a desired temperature of an electrolyte solution and therapeutic agent (20) during electrodeposition processing to deposit a therapeutic agent on a surface of the medical device. In, one example the system can comprise a heat exchanger (30) and a system of pipes or tubing (32, 34) to circulate an electrolyte solution/therapeutic agent (20) or a cooling solution (28) through the heat exchanger (30). In another example, the system can comprise a pump (36) configured to facilitate circulation of an electrolyte solution/therapeutic agent (20), or a cooling solution (28), through a heat exchanger (30) to heat or chill a solution or to maintain a desired temperature of a solution. In another example, the system can comprise a heat exchanger (30) and a system of pipes or tubing (32, 34) configured to circulate an electrolyte solution/therapeutic agent (20) in a first container or a first compartment, or to circulate an electrolyte solution/therapeutic agent (20) in a second container or second compartment, or both, through a heat exchanger (30) to heat or chill a solution or to maintain a desired temperature of the solution during electro-deposition processing. In another example, the system can comprise a pump (36) configured to facilitate circulation of an electrolyte solution/therapeutic agent (20) through a heat exchanger (30). In a preferred example, the system can comprise a heat exchanger (30), a pump (36) and a system of pipes or tubing (32, 34) coupled to the heat exchanger (30) and the pump (36), to circulate an electrolyte solution/therapeutic agent therethrough and to heat or chill the solution or to maintain a desired temperature of the solution during electro-deposition processing.

In one example, a system for depositing a therapeutic agent on a surface of a medical device can also comprise a controller (510) electrically connected to an electrical power supply (500) and to a cathode (18, 18A, 18B) to control sequencing of the application of an electrical signal and/or the timing of the application of a signal to the cathode (18, 18A, 18B). In one example, the cathode (18, 18A, 18B) can be electrically connected by a wire (22) to a controller (510) and the controller can be electrically connected to an electrical power supply (500). In an example, a controller (510) can comprise a switch electrically connected to an electrical power supply (500) and to a cathode (18, 18A, 18B). In another example, a controller can comprise a plurality of switches electrically connected to a plurality of wires (22) that can be electrically connected to a plurality of cathodes, e.g., a first cathode (18A) and a second cathode (18B) of a system. In a preferred example, a plurality of switches can correspond to a plurality of cathodes in a system such that one switch is electrically connected to one of the plurality of cathodes. In yet another example, a controller (510) can comprise a circuit board electrically connected to the cathode (18, 18A, 18B) and to the electrical power supply (500).

In one example, the controller is configured to automatically sequence the application of an electrical signal and/or the timing of the application of an electrical signal to the cathode, or to a plurality of cathodes for systems that include more than one cathode (18, 18A, 18B).

In another example, a system for depositing a therapeutic agent on one or more surfaces of a medical device (100) can comprise a means for data acquisition (600, 610, 620, 630). In one example, the means for data acquisition can comprise one or more sensors or probes (610, 620, 630) for detecting a parameter of a process for depositing a therapeutic agent on a surface of a medical device according to any of the examples disclosed herein. In an example, a sensor or probe can detect a current or amperage (610). In a preferred example, a plurality of probes to detect a current or amperage (610), e.g., a first probe in a first container/compartment (12A, 13A) and a second probe in a second container/compartment (12B, 13B), can be electrically connected to corresponding number of cathodes (18A, 18B), or to a corresponding number of medical devices (100(1), 100(2), etc.) such that one probe is electrically connected to one medical device, and to a controller (510).

In another example, a sensor or probe of the system can detect a voltage (630). In another example, a sensor or probe comprises a plurality of probes to detect a voltage (630), e.g., a voltage to a first cathode (18a) and a second cathode (18b), and the plurality of probes can be electrically connected to a controller (510). In another example, the system can comprise a sensor or probe to detect a temperature of an electrolyte solution (620). In a preferred example, the system comprises a plurality of sensors (620) to detect a temperature of one or more electrolyte solutions/therapeutic agents (20), e.g., to detect a temperature in a first container/compartment (12A, 13A) and to detect a temperature in a second container/compartment (12B, 13B), Data from a sensor or probe (610, 620, 630) can be supplied to a data acquisition device (600), e.g., a monitor, a printer, or a computer or other device configured to record data from a sensor or a probe (610, 620, 630), such that the data can be recorded and/or viewed by a user.

In an example of a method for depositing a therapeutic agent on a surface (10, 14, 14') of a medical device (100), manipulation of a voltage or a current to a cathode during processing (variable cathode methods) can be used with any one or any combination of the examples of systems disclosed herein for electrodeposition of a therapeutic agent on a surface of a medical device. In one example, of a variable cathode electrodeposition method, e.g., in a system generally illustrated in FIG. 4, an electrolyte solution/therapeutic agent (20) can be provided in a volume sufficient to cover a smooth surface (10) of a medical device (100), while a porous surface/modified porous surface (14, 14') of the medical device (100) can initially be excluded from the electrolyte solution/therapeutic agent, such that initial processing will only deposit the therapeutic agent on the smooth surface. In this example, a cathode (18) can initially be fully immersed in the electrolyte solution/therapeutic agent (20). In this example, because a smooth surface (10) requires longer processing to deposit a desired amount of therapeutic agent on the smooth surface (10), and a lower current is drawn during such processing, a larger cathode surface area may be required to deposit a desired concentration of the therapeutic agent on the smooth surface (10) of the medical device, compared to the cathode surface requirements for a porous surface (14, 14'). In one example, the cathode can be immersed in the electrolyte solution/therapeutic agent for a period and the cathode can be partially removed from the electrolyte solution/therapeutic agent (20) to expose a smaller surface area of the cathode (18) to the electrolyte solution/therapeutic agent (20) for processing of the porous surface/modified porous surface (14, 14'), which may more readily adsorb a deposit of the therapeutic agent such that is does not require the same amount of cathode surface area and/or the same period of exposure to an electrolyte solution/therapeutic agent and/or voltage, as required for a smooth surface. In another example, the immersion/removal can be repeated at least twice, preferably multiple times. In another example, an immersion/removal process can be repeated for various periods during the electrolytic reaction. In another example, a cathode (18) can be only partially immersed in an electrolyte solution/therapeutic agent (20), based upon the surface area requirement of the medical device, or the surface area requirement of a select surface (10, 14, 14') of the medical device intended to receive the deposit of therapeutic agent. In another example of a variable cathode method for electrodeposition of a therapeutic agent on a surface of a medical device, a cathode (18) can be switched on for a period and switched off for a period, and this method of switching a cathode on/off can be repeated at least twice during the electrolytic reaction, preferably multiple times during the reaction. In another example, the period during which a cathode is switched on or switched off can be varied during the electrodeposition process to further control deposition of the therapeutic agent. Because a cathode is used to complete an electrical circuit in an electrolytic reaction, varying either the surface area of the cathode exposed to the reaction (e.g., by immersing more or less of the cathode in an electrolyte solution), or switching the cathode on/off at for various periods and/or at various times during the reaction, the amount of a therapeutic agent deposited on a smooth surface (10), a porous surface (14) and/or a modified porous surface comprising micro-pores (14') can be controlled.

There are also provided improved methods to deposit one or more therapeutic agents on a smooth surface (10), and a porous surfaces (14) or a modified porous surfaces comprising micro-pores (14') (e.g., without limitation, as prepared according to the modified micro-arc oxidation methods describe herein) of a medical implant, simultaneously, by using different cathodes and/or different electrolyte solutions for the smooth surface (10) and the porous surface (14, 14') to thereby create separate electrolytic reactions at the smooth surface and porous surface, e.g., by providing separate containers or a divided container comprising compartments for holding separate electrolyte solutions/therapeutic agents and/or separate cathodes. The amount of the therapeutic agent deposited on the smooth surface and porous surface can also be controlled by using a variable cathode method as described herein.

In one example, as illustrated in FIGS. 12A, 12B and 12C, a method of using electrodeposition to deposit a therapeutic agent on a medical device having a smooth surface (10) and a porous surface (14) or a modified porous surface comprising micro-pores (14'), includes providing an electrolytic cell comprising a container (12, 12A, 12B, 13A, 13B), an electrolyte solution and therapeutic agent (20), a cathode (18, 18A, 18B), and an anode comprising the medical device (100), applying an electrical signal (voltage) to the electrolytic cell, and manipulating the voltage to the cathode during the electrolytic reaction to control the deposit of the therapeutic agent on at least one of the smooth surface (10) and the porous surface or a modified porous surface (14, 14') of the medical device (100). In another example, the method can comprise providing an electrolytic cell comprising a container (12, 12A, 12B, 13A, 13B), an electrolyte solution and the therapeutic agent (20), a cathode (18, 18A, 18B), and an anode comprising the medical device (100), applying an electrical signal (voltage) to the electrolytic cell, and manipulating a current created during the electrolytic reaction to control the deposit of the therapeutic agent on at least one of the smooth surface (10) and the porous surface or modified porous surface (14, 14') of the medical device. In one example, the current can be manipulated by decreasing or increasing the surface area of a cathode (18, 18A, 18B) that is exposed to the electrolyte solution/therapeutic agent (20) during the reaction. In another example, manipulating the voltage includes switching a cathode on for a period and off for a period, and repeating the switching on/off (such that it is switched on/off at least twice), during an electrolytic reaction.

In another example, a method of electrodeposition of a therapeutic agent on a surface of a medical device can comprise a performing the electrodeposition process in an electrolytic cell having a container comprising a first container or first compartment (12A, 13A) and a second container or second compartment (12B, 13B), and a cathode (18) can comprise a first cathode (18A) disposed in the first container or first compartment and a second cathode (18B) disposed in the second container or second compartment, and applying the voltage comprises applying a first voltage to the first cathode and applying a second voltage to the second cathode, the second voltage being different from the first voltage. In one example, the electrolyte solution/therapeutic agent (20) is the same in the first electrolyte solution/therapeutic agent in the first compartment. In another example, the method can include using a first electrolyte solution or first therapeutic agent in the first container or first compartment (12A, 13A), and using a second electrolyte solution or a second therapeutic agent in the second container or second compartment (12B, 13B), the second electrolyte solution being different from the first electrolyte solution or the second therapeutic agent being different from the first therapeutic agent. In another example, the method can further comprise circulating the first electrolyte solution/therapeutic agent, the second electrolyte solution/therapeutic agent, or both, through a temperature regulating device configured to maintain a temperature of the first electrolyte solution, the second electrolyte solution, or both. In one example, both the first electrolyte solution/therapeutic agent and the second electrolyte solution/therapeutic agent are circulated through a temperature regulating device to maintain the respective temperature of the first electrolyte solution/therapeutic agent and the second electrolyte solution/therapeutic agent. In a preferred example, an electrolyte solution/therapeutic agent for processing a smooth surface can be provided and maintained at a temperature between room temperature (e.g., about 25° C.) to about 50° C., preferably about 40° C. In another preferred example, an electrolyte solution/therapeutic agent for processing a porous surface (14) or a modified porous surface comprising micro-pores (14') can be provided and maintained at a temperature of about 10° C. or less, preferably about 5° C. or less, most preferably 2° C. or less.

In another example of a method for electrodeposition of a therapeutic agent on a medical device comprising a smooth surface and a porous surface or a modified porous surface, can include providing an electrolytic cell comprising a first container configured to receive the smooth surface of the device, the first container comprising a first electrolyte solution/therapeutic agent and a first cathode; providing a second container configured to receive the porous surface or modified porous surface of the medical device, the second container comprising a second electrolyte solution/therapeutic agent and a second cathode; and a temperature regulating device configured to maintain a temperature of the first electrolyte solution/therapeutic agent, the temperature of the second electrolyte solution/therapeutic agent, or both.

One of ordinary skill in the art will understand that applying an electrical signal to an electrolytic cell in any of the above-described methods for electrodeposition of a therapeutic agent on a surface of a medical device can employ any electrical signal suitable for the therapeutic agent, the electrolyte solution and the medical device. For example, the electrical signal can comprise any peak voltage, any waveform, any frequency (duty cycle), and any period of application time generally known for use in electrodeposition, or generally known for use in a micro-arc oxidation process, or known for modified micro-arc oxidation as described in this disclosure, provided that such parameters are suitable for the therapeutic agent, the electrolyte solution, and the medical device.

In one example, the system and method for processing a plurality of medical devices in a single electrolyte solution using a micro-arc oxidation process, can also be used for processing a plurality of medical devices to deposit a therapeutic agent on a surface of each one of the plurality of medical devices.

EXAMPLES

Example 1

Porous Plasma Sprayed (PPS) titanium alloy discs of 2 cm diameter and 2 mm thickness were evaluated for their ability to inhibit bacterial growth. PPS discs were either non-anodized for use as a control, or oxidized by using the modified micro-arc oxidation process according to an example described above to produce micro-porous surfaces, and either left untreated or treated with iodine according an example of a method of depositing a therapeutic agent on a surface of a medical device as described herein and as illustrated in FIG. 12B, producing discs having between 8 $\mu g/cm^2$ and 16 $\mu g/cm^2$ iodine. These control and anodized discs were then tested for antimicrobial testing in accordance with JIS Z 2801:2010, *Antibacterial products—Test for antibacterial activity and efficacy*, commonly known as the Japanese film method test. A predefined bacterial inoculum concentration of *Staphylococcus aureus* bacteria was deposited on the discs and the discs were then covered with glass coverslip. The discs were incubated at 37° C. for 24 hours. The bacteria from the discs and the coverslips was then recovered by sonication and rinsing of the discs and coverslips, and the resulting bacterial extracts were plated on agar. The colony forming units (CFU) formed on the agar plates were counted as shown in FIG. 14. Non-anodized discs demonstrate bacterial growth. The bacteria recovered from the discs treated with the modified micro-arc oxidation process demonstrate reduced numbers of bacteria, and discs treated with the modified micro-arc oxidation process and the iodine deposition process described above demonstrate substantial reduction in bacteria.

Definitions

Although the terms first, second, third, etc. may be used herein to describe various elements, components, regions, layers and/or sections, these elements, components, regions, layers and/or sections should not be limited by these terms.

These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of manufacturing a medical device, comprising:

securing an electrode to a metallic substrate in an electrolyte solution, wherein the metallic substrate includes a porous layer and a non-porous layer, wherein the porous layer is configured to facilitate tissue in-growth or tissue on-growth;

providing a cathode in the electrolyte solution;

applying a voltage to the metallic substrate to form a plurality of micro-pores on the porous layer by micro-arc oxidation; and simultaneously depositing a therapeutic agent on the non-porous layer and on the porous layer of the metallic substrate in the plurality of micro-pores;

wherein depositing the therapeutic agent comprises electrophoretic deposition or electrodeposition of the therapeutic agent.

2. The method of claim 1, wherein applying the voltage includes using a controller to control the voltage and timing of application of the voltage to the metallic substrate, wherein the controller comprises a switch, a circuit board, a relay, or a combination thereof.

3. The method of claim 1, further comprising circulating the electrolyte solution through a temperature regulating device to maintain a temperature of the electrolyte solution within a desired range while applying the voltage.

4. The method of claim 1, wherein the porous layer comprises an anode of an electrolytic cell and the cathode of the electrolytic cell is in the electrolyte solution.

5. The method of claim 1, wherein depositing the therapeutic agent on the porous layer having the plurality of micro-pores includes switching the voltage to the cathode on and off at least twice, and wherein depositing the therapeutic agent comprises electrophoretic deposition or electrodeposition of the therapeutic agent in a second electrolyte solution.

6. A method of manufacturing a medical device, comprising:

securing an electrode to a metallic substrate in an electrolyte solution, wherein the metallic substrate includes a porous layer and a non-porous layer, wherein the porous layer is configured to facilitate tissue in-growth or tissue on-growth;

providing a cathode in the electrolyte solution;

applying a voltage to the metallic substrate to form a plurality of micro-pores on the porous layer by micro-arc oxidation; and depositing a therapeutic agent on the non-porous layer and on the porous layer of the metallic substrate in the plurality of micro-pores;

wherein depositing the therapeutic agent comprises electrophoretic deposition or electrodeposition of the therapeutic agent and wherein depositing the therapeutic agent includes performing a second depositing process to deposit the therapeutic agent on the non-porous layer.

7. The method of claim 6, further comprising applying a first voltage to the porous layer and applying a second voltage to the non-porous layer, wherein the first voltage is different from the second voltage.

8. The method of claim 1, wherein the plurality of micro-pores are treated by acid etching.

9. A method of manufacturing a medical device, comprising:

securing an electrode to a metallic substrate in an electrolyte solution, wherein the metallic substrate includes a porous layer and a non-porous layer;

providing a cathode in the electrolyte solution; and applying a voltage to the metallic substrate to form a plurality of micro-pores on a porous layer of the metallic substrate by micro-arc oxidation, wherein the porous layer is configured to facilitate tissue in-growth or tissue on-growth;

circulating the electrolyte solution through a temperature regulating device to maintain a temperature of the electrolyte solution within a desired temperature range while applying the voltage;

depositing a therapeutic agent on the plurality of micro-pores on the metallic substrate; and manipulating the voltage to the cathode or manipulating a current to control depositing of the therapeutic agent;

wherein manipulating the voltage to the cathode or manipulating the current to control depositing of the therapeutic agent includes controlling the depositing to achieve a desired amount or concentration of the therapeutic agent absorbed by the porous layer and by the non-porous layer.

10. The method of claim 9, wherein the voltage during the micro-arc oxidation has a root mean square of 200V.

11. The method of claim 9, wherein manipulating the voltage includes switching the cathode on and off at least twice.

12. The method of claim 1, wherein the electrolyte solution is maintained at temperature of 0° C. to 50° C.

13. The method of claim 1, wherein the therapeutic agent includes iodine compounds having a concentration of between 1% to about 10%, by weight or by volume.

14. The method of claim 1, further comprising applying heat to dry the medical device.

15. The method of claim 1, further comprising applying a voltage to the non-porous layer in a sequence with applying the voltage to the metallic substrate to form the plurality of micro-pores in the porous layer by micro-arc oxidation.

16. The method of claim 1, further comprising applying a voltage to the non-porous layer received in the electrolyte solution with the porous layer.

17. The method of claim 1, wherein depositing the therapeutic agent on the non-porous layer and on the porous layer of the metallic substrate in the plurality of micro-pores includes controlling the depositing to achieve a desired amount or concentration of the therapeutic agent absorbed by the porous layer and by the non-porous layer.

18. The method of claim 9, wherein manipulating the voltage to the cathode or manipulating the current includes applying an alternating current as a rectified sine wave.

19. The method of claim 9, wherein maintaining the temperature of the electrolytic solution includes continuously withdrawing the electrolyte solution from a container through at least a first pipe and continuously adding the electrolyte solution that has been cooled to the desired temperature range through at least a second pipe to the container.

20. The method of claim 9, further comprising applying a voltage to the non-porous layer received in the electrolyte solution with the porous layer.

21. The method of claim 9, further comprising applying a voltage to the non-porous layer in a sequence with applying the voltage to the metallic substrate to form the plurality of micro-pores on the porous layer of the metallic substrate by micro-arc oxidation.

\* \* \* \* \*